US012667506B2

(12) United States Patent
Zerhusen et al.

(10) Patent No.: US 12,667,506 B2
(45) Date of Patent: Jun. 30, 2026

(54) PATIENT SUPPORT SYSTEM WITH TRANSFERABLE SUPPORT SURFACE

(71) Applicant: Hill-Rom Services, Inc., Batesville, IN (US)

(72) Inventors: Robert Mark Zerhusen, Cincinnati, OH (US); Nicholas A. Mann, Cincinnati, OH (US); David C. Newkirk, Lawrenceburg, IN (US); Todd P. O'Neal, Fairfield, OH (US); Jack Barney Sing, Batesville, IN (US); Neal Wiggermann, Batesville, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 0 days.

(21) Appl. No.: 18/748,277

(22) Filed: Jun. 20, 2024

(65) Prior Publication Data

US 2024/0423853 A1 Dec. 26, 2024

Related U.S. Application Data

(60) Provisional application No. 63/522,754, filed on Jun. 23, 2023.

(51) Int. Cl.
*A61G 7/10* (2006.01)
*A61F 7/00* (2006.01)

(52) U.S. Cl.
CPC ............ *A61G 7/1026* (2013.01); *A61F 7/007* (2013.01); *A61F 2007/006* (2013.01); *A61F 2007/0064* (2013.01); *A61F 2007/0075* (2013.01)

(58) Field of Classification Search
None
See application file for complete search history.

(56) References Cited

U.S. PATENT DOCUMENTS 6,341,393 B1 1/2002 Votel
6,378,148 B1 4/2002 Votel
(Continued)

FOREIGN PATENT DOCUMENTS

EP 2415444 A2 8/2012
WO 2021006799 A1 1/2021
WO 2022211710 A1 10/2022

OTHER PUBLICATIONS

Hovertech International, Hoversling Repositioning Sheet, Multi-functional to Streamline Process, https://hovermatt.com/products/hoversling-repositioning-sheet/; Available at least as early as Jun. 8, 2020.

(Continued)

*Primary Examiner* — Adam C Ortiz
(74) *Attorney, Agent, or Firm* — Price Heneveld LLP

(57) ABSTRACT

A patient support system includes a frame assembly and a support surface system configured to support a person thereon. The support surface system includes a surface assembly including a spacer material and a thermoelectric device and a control assembly including a blower and a power source. A tether is coupled to the control assembly and the surface assembly. The tether includes an airflow channel and an electrical connection. A controller is communicatively coupled to the support surface system. The controller is configured to selectively activate a blower to direct air through the airflow channel and through the spacer material to form a microclimate management layer in the surface assembly and selectively activate a power source to drive a current through the thermoelectric device for temperature regulation.

18 Claims, 19 Drawing Sheets

(56)     References Cited

U.S. PATENT DOCUMENTS

| | | | |
|---|---|---|---|
| 6,834,402 | B2 | 12/2004 | Hanson et al. |
| 7,114,203 | B2 | 10/2006 | Lloyd et al. |
| 7,243,382 | B2 | 7/2007 | Weedling et al. |
| 7,340,784 | B2 | 3/2008 | Stryker et al. |
| 7,739,758 | B2 | 6/2010 | Weedling et al. |
| 9,730,847 | B2 | 8/2017 | Lachenbruch et al. |
| 10,500,115 | B2 | 12/2019 | Weedling |
| 11,206,928 | B2 | 12/2021 | Dorshorst |
| 11,324,650 | B2 | 5/2022 | Zhou et al. |
| 11,400,002 | B2 | 8/2022 | Lewis |
| 2006/0243720 | A1 | 11/2006 | Koch et al. |
| 2010/0235986 | A1 | 9/2010 | Klyne et al. |
| 2010/0281613 | A1 | 11/2010 | Hillenbrand, II |
| 2013/0073012 | A1 | 3/2013 | Ellis |
| 2017/0231847 | A1 | 8/2017 | Hillenbrand, II et al. |

OTHER PUBLICATIONS

Hillrom, RepoSheet Patient LiftAid by RepotSheet, https://www.hillrom.com/en/products/reposheet-lift-aid; Jun. 12, 2023.

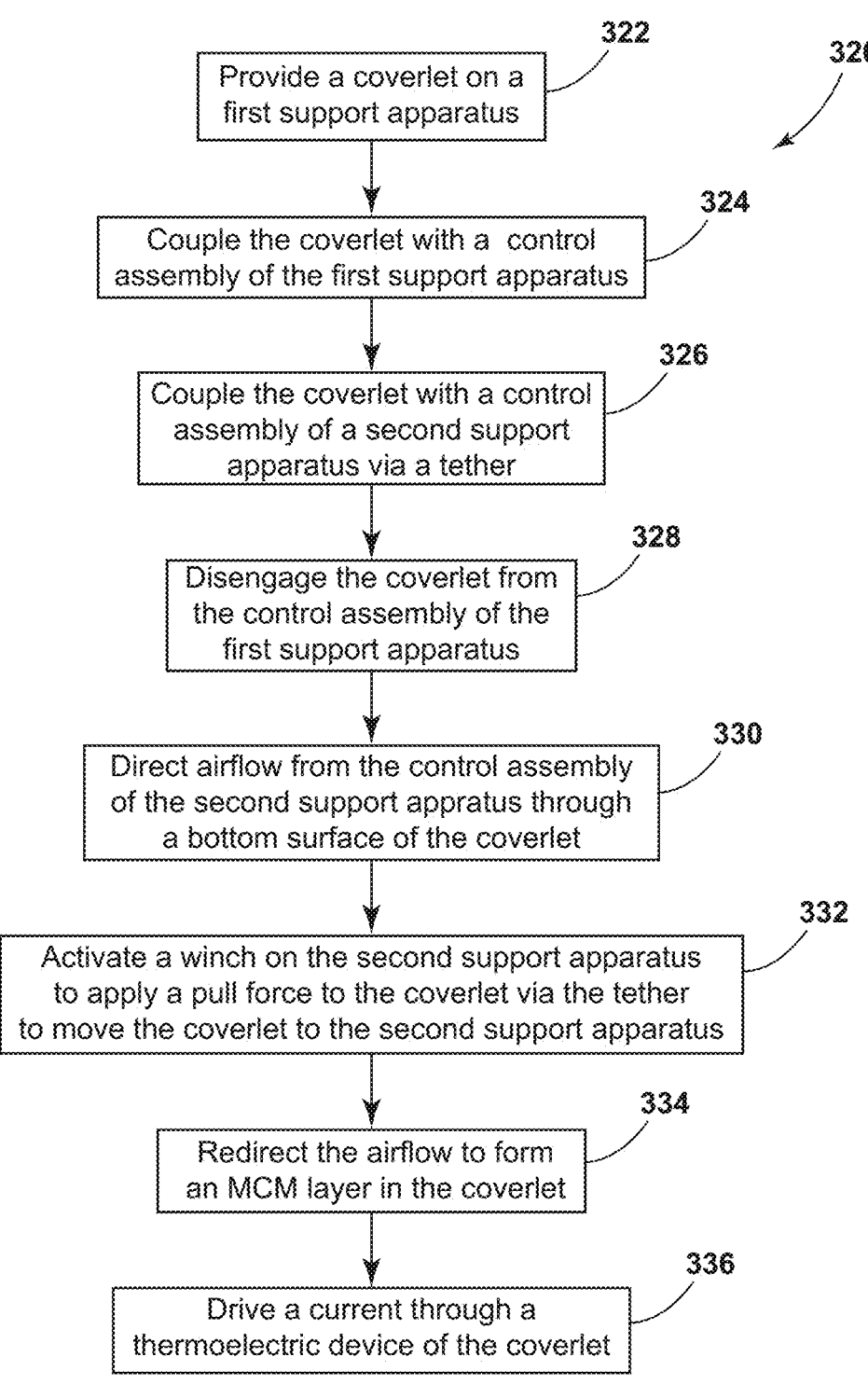

322
Provide a coverlet on a
first support apparatus

320

324
Couple the coverlet with a control
assembly of the first support apparatus

326
Couple the coverlet with a control
assembly of a second support
apparatus via a tether 328
Disengage the coverlet from
the control assembly of the
first support apparatus 330
Direct airflow from the control assembly
of the second support appratus through
a bottom surface of the coverlet 332
Activate a winch on the second support apparatus
to apply a pull force to the coverlet via the tether
to move the coverlet to the second support apparatus 334
Redirect the airflow to form
an MCM layer in the coverlet 336
Drive a current through a
thermoelectric device of the coverlet

FIG. 19

PATIENT SUPPORT SYSTEM WITH TRANSFERABLE SUPPORT SURFACE

CROSS-REFERENCE TO RELATED APPLICATION

This application claims priority to and the benefit under 35 U.S.C. § 119(e) of U.S. Provisional Application No. 63/522,754, filed on Jun. 23, 2023, entitled "PATIENT SUPPORT SYSTEM WITH TRANSFERABLE SUPPORT SURFACE," the disclosure of which is hereby incorporated herein by reference in its entirety.

FIELD OF THE DISCLOSURE

The present disclosure generally relates to a patient support system, and more particularly to a patient support system with a transferable therapy surface assembly.

SUMMARY OF THE DISCLOSURE

According to one aspect of the present disclosure, a patient support system includes a frame assembly. A support surface system is selectively supported by the frame assembly and configured to support a person thereon. The support surface system includes a surface assembly including a spacer material and a thermoelectric device within an interior of the surface assembly and a control assembly including a blower and a power source. A tether is coupled to the control assembly and the surface assembly. The tether includes an airflow channel in fluid communication with the blower and an interior of the surface assembly. The tether includes an electrical connection operably coupled with the power source and the thermoelectric device. A controller is communicatively coupled to the support surface system. The controller is configured to selectively activate the blower to direct air through the airflow channel and through the spacer material to form a microclimate management layer in the surface assembly and selectively activate the power source to drive a current through the thermoelectric device for temperature regulation.

According to an aspect of the present disclosure, a patient support system includes a support apparatus including a frame assembly. A control assembly is coupled to the frame assembly. The control assembly includes a blower, a power source, and a winch. A coverlet is selectively disposed on the frame assembly. The coverlet includes a spacer material and a thermoelectric device. A tether is coupled to the control assembly and selectively coupled to the coverlet. The tether includes an airflow channel for directing air from the blower to an interior of the coverlet and an electrical connection coupling the power source with the thermoelectric device. A controller is communicatively coupled to the control assembly. The controller is configured to activate the blower to direct the air through the airflow channel and through an interior of the coverlet, activate the power source to drive a current through the thermoelectric device, and activate the winch to move the coverlet relative to the frame assembly.

According to an aspect of the present disclosure, a patient support system includes a first support apparatus. A coverlet includes a spacer material and a thermoelectric device. The coverlet is selectively disposed on the first support apparatus. The second support apparatus includes a control assembly including a blower, a power source, and a winch. A tether is coupled to the control assembly and configured to selectively couple to the coverlet. The tether includes an airflow channel for directing air from the blower to an interior of the coverlet and an electrical connection coupling the power source to the thermoelectric device. A controller is communicatively coupled to the control assembly. The controller is configured to activate the winch to provide a pulling force on the coverlet to move the coverlet from the first support apparatus to the second support apparatus.

According to an aspect of the present disclosure, a patient support apparatus includes a frame assembly. A first control subassembly is coupled to the frame assembly on a first side. The first control subassembly includes a first tether including an airflow channel and an electrical connection. A first blower is configured to direct air through the airflow channel. A first power source is configured to drive a current through the electrical connection. A first winch is coupled to the first tether and configured to adjust the first tether. A second control subassembly is coupled to the frame assembly on a second side. The second control subassembly includes a second tether including an airflow channel and an electrical connection. A second blower is configured to direct air through the airflow channel of the second tether. A second power source is configured to drive a current through the electrical connection of the second tether. A second winch is coupled to the second tether and configured to adjust the second tether.

According to one aspect of the present disclosure, a support surface system includes a surface assembly including an outer covering, a spacer material disposed within the outer covering, and a thermoelectric device disposed within the outer covering. A control assembly is operably coupled to the surface assembly. The control assembly includes a blower and a power source. A tether includes an airflow channel in fluid communication with the blower and an interior of the outer covering and an electrical connection in communication with the power source and the thermoelectric device. A controller is communicatively coupled to the control assembly. The controller is configured to selectively activate the blower to direct air through the airflow channel and through the spacer material to form a microclimate management layer in the surface assembly and selectively activate the power source to drive a current through the thermoelectric device for temperature regulation.

According to an aspect of the present disclosure, a method of transferring a patient between support apparatuses includes providing a coverlet on a first support apparatus; coupling the coverlet with a control assembly of a second support apparatus, the control assembly including a blower, a power source, and a winch, where the second support apparatus is disposed adjacent to the first support apparatus; directing an airflow from the blower through a bottom surface of the coverlet; activating the winch to provide a pull force on the coverlet to move the coverlet from the first support apparatus to the second support apparatus; redirecting the airflow through a spacer material of the coverlet to form a microclimate management layer; and driving a current through a thermoelectric device of the coverlet to provide temperature regulation.

These and other features, advantages, and objects of the present disclosure will be further understood and appreciated by those skilled in the art by reference to the following specification, claims, and appended drawings.

BRIEF DESCRIPTION OF THE DRAWINGS

In the drawings:

FIG. 19 is a flow diagram of a method for transferring a patient between support apparatuses, according to the present disclosure.

DETAILED DESCRIPTION

Figure 1:
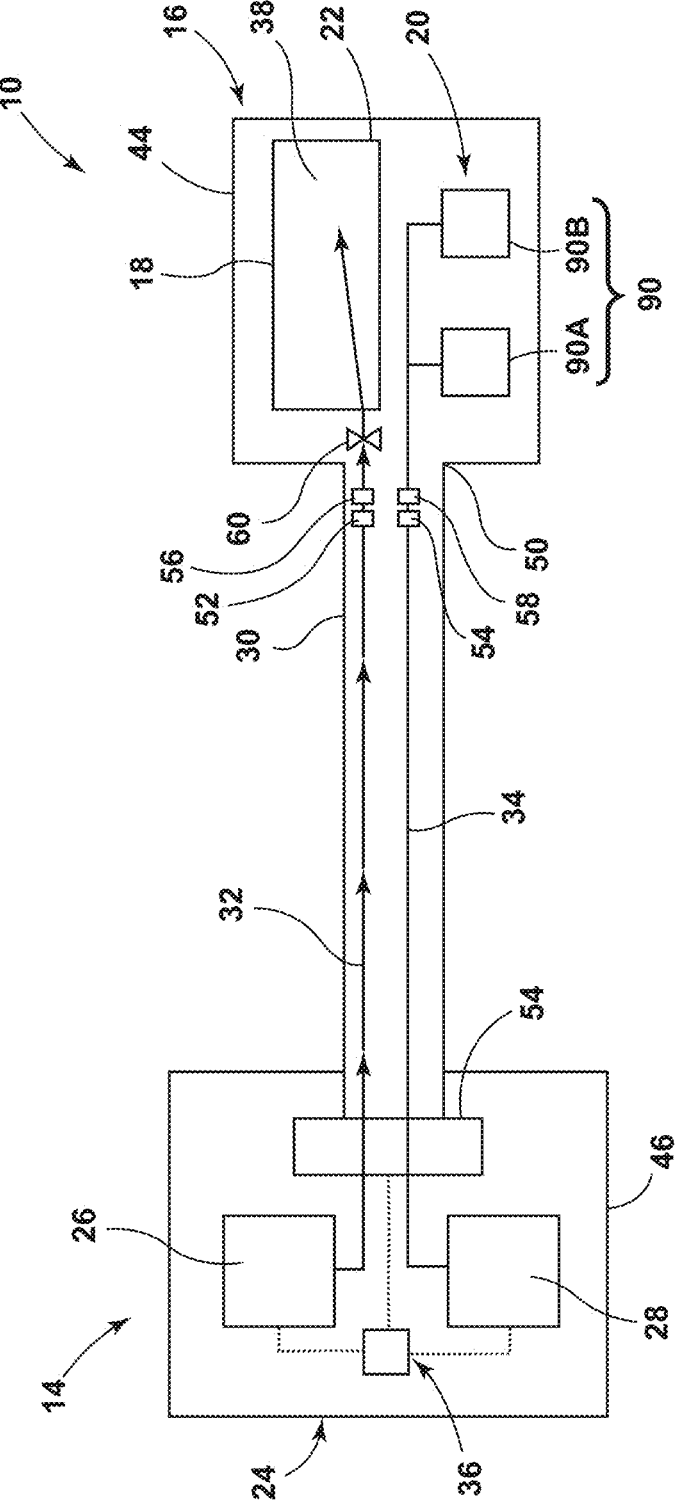
FIG. 1 is a schematic diagram of a support surface system with a control assembly, a tether, and a surface assembly, according to the present disclosure.

The present illustrated embodiments reside primarily in combinations of method steps and apparatus components related to a patient support surface with a transferrable support surface. Accordingly, the apparatus components and method steps have been represented, where appropriate, by conventional symbols in the drawings, showing only those specific details that are pertinent to understanding the embodiments of the present disclosure so as not to obscure the disclosure with details that will be readily apparent to those of ordinary skill in the art having the benefit of the description herein. Further, like numerals in the description and drawings represent like elements.

For purposes of description herein, the terms "upper," "lower," "right," "left," "rear," "front," "vertical," "horizontal," and derivatives thereof, shall relate to the disclosure as oriented in FIG. 1. Unless stated otherwise, the term "front" shall refer to a surface closest to an intended viewer, and the term "rear" shall refer to a surface furthest from the intended viewer. However, it is to be understood that the disclosure may assume various alternative orientations, except where expressly specified to the contrary. It is also to be understood that the specific structures and processes illustrated in the attached drawings, and described in the following specification are simply exemplary embodiments of the inventive concepts defined in the appended claims. Hence, specific dimensions and other physical characteristics relating to the embodiments disclosed herein are not to be considered as limiting, unless the claims expressly state otherwise.

The terms "including," "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element preceded by "comprises a . . . " does not, without more constraints, preclude the existence of additional identical elements in the process, method, article, or apparatus that comprises the element.

With reference to FIGS. 1-19, reference numeral 10 generally designates a patient support system 10 that includes a frame assembly 12 and a support surface system 14 selectively supported by the frame assembly 12 and configured to support a person therein. The support surface system 14 includes a surface assembly 16 with a spacer material 18 and a thermoelectric device 20 within an interior 22 of the surface assembly 16, and a control assembly 24 that includes a blower 26 and a power source 28. A connector, belt, or tether 30 is coupled to the control assembly 24 and the surface assembly 16. The tether 30 includes an airflow channel 32 in fluid communication with the blower 26 and the interior 22 of the surface assembly 16. The tether 30 also includes an electrical connection 34 operably coupled with the power source 28 and the thermoelectric device 20. A controller 36 is communicatively coupled to the support surface system 14. The controller 36 is configured to selectively activate the blower 26 to direct air through the airflow channel 32 and through the spacer material 18 to form a microclimate management layer 38 in the surface assembly 16 and selectively activate the power source 28 to drive a current through the thermoelectric device 20 for temperature regulation.

Figure 2:
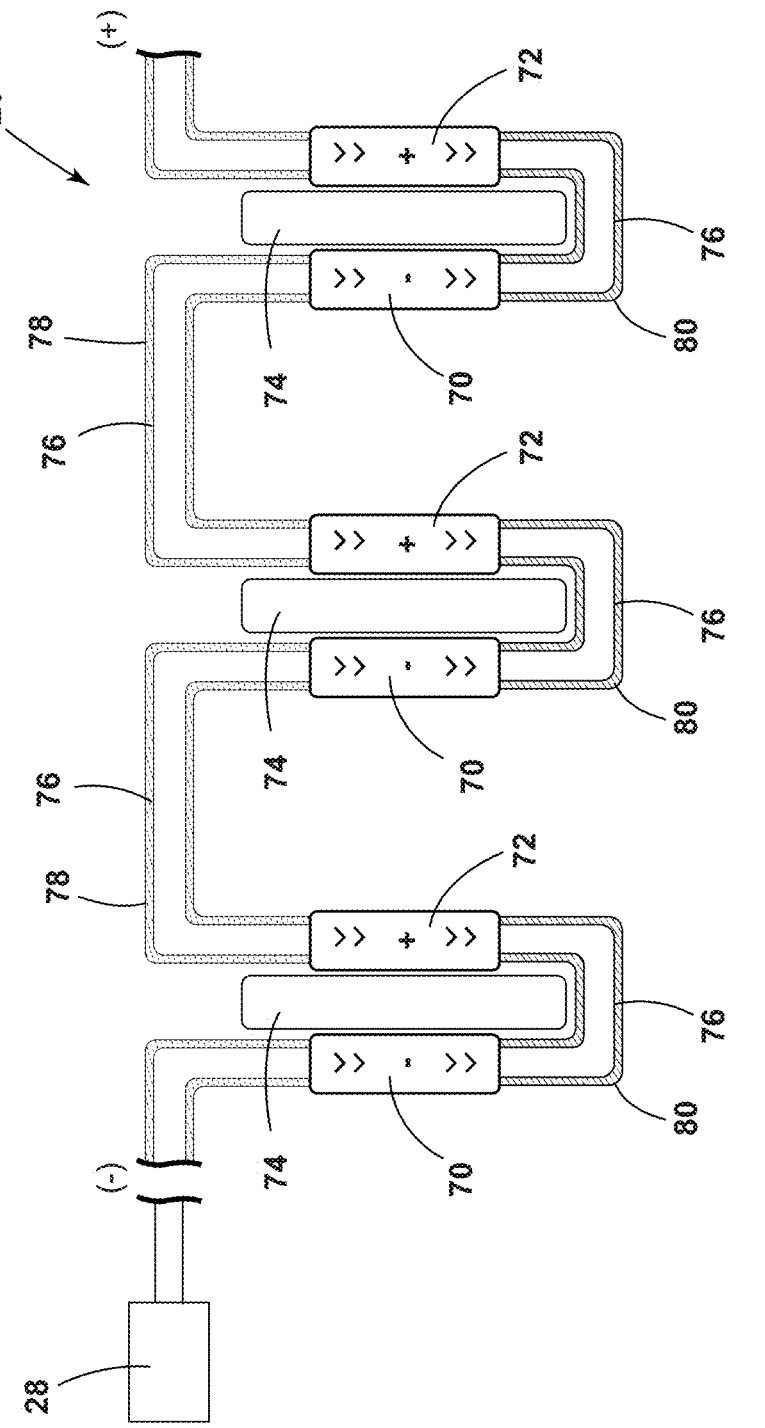
FIG. 2 is a partial side elevational cross-sectional view of a thermoelectric device for a support surface system, according to the present disclosure.

With reference to FIGS. 1 and 2, the surface assembly 16 includes an outer covering 44, also referred to as a ticking or outer ticking, defining the interior 22. The spacer material 18 is disposed within the interior 22 and is constructed of a material that permits airflow therethrough. The surface assembly 16 also includes the thermoelectric device 20 disposed within the interior 22. The thermoelectric device 20 may be in a separate layer compared to the spacer material 18 or may be integrated or woven into the spacer material 18. Additionally or alternatively, the spacer material 18 and the thermoelectric device 20 may be disposed adjacent to one another, aligning with same or different areas on the patient to provide different treatments. The spacer material 18 and the thermoelectric device 20 may be formed and/or arranged to be flexible to conform to a specific shape or configuration for supporting the patient.

The surface assembly 16 is coupled to the control assembly 24 via the tether 30, which provides communication between the control assembly 24 and the surface assembly 16. The control assembly 24 may include multiple components disposed in or coupled to a housing 46 or may be multiple components disposed adjacent to one another (e.g., without the housing 46 or some components outside the housing 46). The housing 46 may be advantageous for providing a modular support surface system 14. The control assembly 24 includes the blower 26 for directing air and the power source 28 for providing a voltage and driving an electric current. In various examples, the control assembly 24 also includes a winch 48 for adjusting a length of the tether 30 and for providing movement of the surface assembly 16.

The tether 30 includes or defines the airflow channel 32, which provides fluid communication between the control assembly 24 and the interior 22 of the surface assembly 16. The tether 30 also includes the electrical connection 34, which provides electrical communication between the power source 28 and the thermoelectric device 20. The tether 30 is generally configured as a vinyl belt but may have a variety of configurations.

In certain aspects, the tether 30 is fixedly coupled to the components of the control assembly 24, including one or more of the blower 26, the power source 28, and the winch 48. The tether 30 is generally selectively attached to and detached from the surface assembly 16. This may be advantageous for the transfer of the patient utilizing different control assemblies 24 for the surface assembly 16, as described herein, for cleaning, for storage, etc. The tether 30 includes a connector end 50 for selectively engaging and disengaging the surface assembly 16 and the components therein. The connector end 50 may be configured to clamp to, insert in, or otherwise engage with the surface assembly 16. Moreover, the connector end 50 may include a power connection valve 52 and an air connection valve 54 for coupling the electrical connection 34 and the airflow channel 32 with a power connection valve 56 and an air connection valve 58 in the surface assembly 16. Generally, the connection valves 52, 54, 56, 58 are mating, quick disconnect valves allowing for efficient engagement and disengagement between the connector end 50 and the surface assembly 16.

With reference still to FIGS. 1 and 2, when the air connection valves 54, 58 are connected, the air is directed in a select direction through the surface assembly 16. Generally, the air is directed through the spacer material 18 for providing climate or microclimate management for the patient, which may be referred to as the microclimate management or MCM layer 38. The blower 26 operates to direct or blow air through the airflow channel 32 and through the spacer material 18. The patient may rest on the MCM layer 38, and while the patient is positioned on the MCM layer 38, the air is directed through the spacer material 18. This configuration wicks away moisture from the skin of the patient by blowing air underneath the patient, which is advantageous for preventing skin conditions that may be caused by being positioned on the surface assembly 16 for an extended period of time.

Additionally, in various examples, the support surface system 14 may include a re-directing valve 60, which is configured to redirect the air in the surface assembly 16. The re-directing valve 60 may be included in the air connection valve 58, in the surface assembly 16, or in the tether 30. In such examples, as described further herein, the air may be directed in multiple directions, including in a first direction for the MCM layer 38 and in a second direction through the outer covering 44. The outer covering 44 may include a designated top surface 62 configured to contact the patient and a designated bottom surface 64, opposing the top surface 62. The air may be redirected through the bottom surface 64 of the outer covering 44, which may assist in providing a "hover" or "hover-like" effect for the surface assembly 16 to assist in patient transfer. The re-directing valve 60 may also control a strength of the airflow through the surface assembly 16, which may increase moisture-wicking treatments and/or increase the strength of the "hover" effect.

Referring still to FIGS. 1 and 2, the surface assembly 16 is also configured to provide temperature regulation for the patient with the thermoelectric device 20. The thermoelectric device 20 may include multiple p- and n-connectors, which are configured to generate heat flux across junctions 74. The temperature difference generated through the Peltier effect is generally created by transferring heat between two junctions 74. The semiconductors 70, 72 may be arranged in an alternating pattern and coupled via electrical connectors 76. The thermoelectric device 20 may include any practicable number of the semiconductors 70, 72, junctions 74, and electrical connectors 76. The thermoelectric device 20 may form an elongated feature extending along, through, or adjacent to the spacer material 18. In certain aspects, the thermoelectric device 20 may form a pattern such as a serpentine pattern across the surface assembly 16.

In a non-limiting example, the thermoelectric device 20 operates via the Peltier effect. When the voltage is applied to the semiconductors 70, 72 to direct the current in a first direction, a first side 78 of the thermoelectric device 20 is a cold side while a second opposing side 80 is a heated side. When the current is directed in an opposing direction, the first side 78 is heated and the second side 80 is cold. The thermoelectric device 20 is operably coupled with the power source 28 for providing voltage to the thermoelectric device 20 and generating the heat flux. The changing of the heated and cooled sides 78, 80 may be advantageous for selectively heating and cooling areas of the patient with the same thermoelectric modules 90 at different times.

The thermoelectric device 20 may be associated with a designated airflow channel 32 and/or the airflow formed by the blower 26 in the MCM layer 38. Air may be directed past the thermoelectric device 20 to move the heated or cooled air out of the thermoelectric device 20. For example, when the second side 80 of the thermoelectric device 20 is positioned within the airflow path, the first side 78 is arranged proximate to the patient to provide temperature regulation for the patient. In this way, the temperature of the first side 78 produces the temperature effect felt by the patient while the temperature effect from the second side 80 is directed away from the patient by the airflow.

For example, when the thermoelectric device 20 is being used to cool the patient, the first side 78 (i.e., the patient-facing side) is cooled and the second side 80 (i.e., the floor-facing side away from the patient) is heated. The heat is then directed away from and out of the surface assembly 16. The blower 26, which provides the MCM layer 38, can be utilized to move air and exhaust the heat from the thermoelectric device 20. The movement of the air and the heat may be accomplished via an air-permeable ticking or outer covering 44 on the surface assembly 16, holes in the bottom surface 64 of the surface assembly 16, additional vents for heat exhaustion (e.g., smaller vents with an envelope-like cover), or combinations thereof. In certain aspects, the blower 26 may generate the airflow through the spacer material 18 for the MCM layer 38 and a separate airflow for the thermoelectric device 20, such as through the air connection valve 58 or the re-directing valve 60. This configuration may be advantageous for having the airflow for the MCM layer 38 closer to the patient to provide moisture wicking, and the airflow for the thermoelectric device 20 further from the patient to not impinge on the temperature regulation felt by the patient. Similar methods for moving the air through the surface assembly 16 are used for the MCM layer 38 to provide airflow and exhaust moisture.

It is contemplated that other thermoelectric devices 20 or alternate configurations of the thermoelectric device 20 may be utilized without departing from the teachings herein. For example, the thermoelectric device 20 may include conductive spacer material and a fan, where the fan is configured to draw heat away from the conductive spacer material and, accordingly, away from the patient. Moreover, the thermoelectric device 20 may include or be configured as one or more resistive heaters to generate heat to warm the patient.

In the example illustrated in FIG. 1, the thermoelectric device 20 includes multiple thermoelectric modules 90, such as the thermoelectric modules 90A, 90B. Any practicable number of thermoelectric modules 90 may be included in the surface assembly 16. The thermoelectric modules 90 may be selectively and independently activated, deactivated, and controlled to provide different temperature regulations. In such examples, the thermoelectric modules 90 may be controlled based on the location of the thermoelectric modules 90 in the surface assembly 16 and the area of the patient to which the thermoelectric modules 90 align. For example, areas on the patient with a higher likelihood of developing a pressure injury from an extended period on the surface assembly 16, such as the sacral region, ischial tuberosity, or heels, may be cooled, while other areas of the body may be heated to provide comfort for the patient. Further, different areas can be heated or cooled for different lengths of time, at different intensities, etc.

Figure 3:
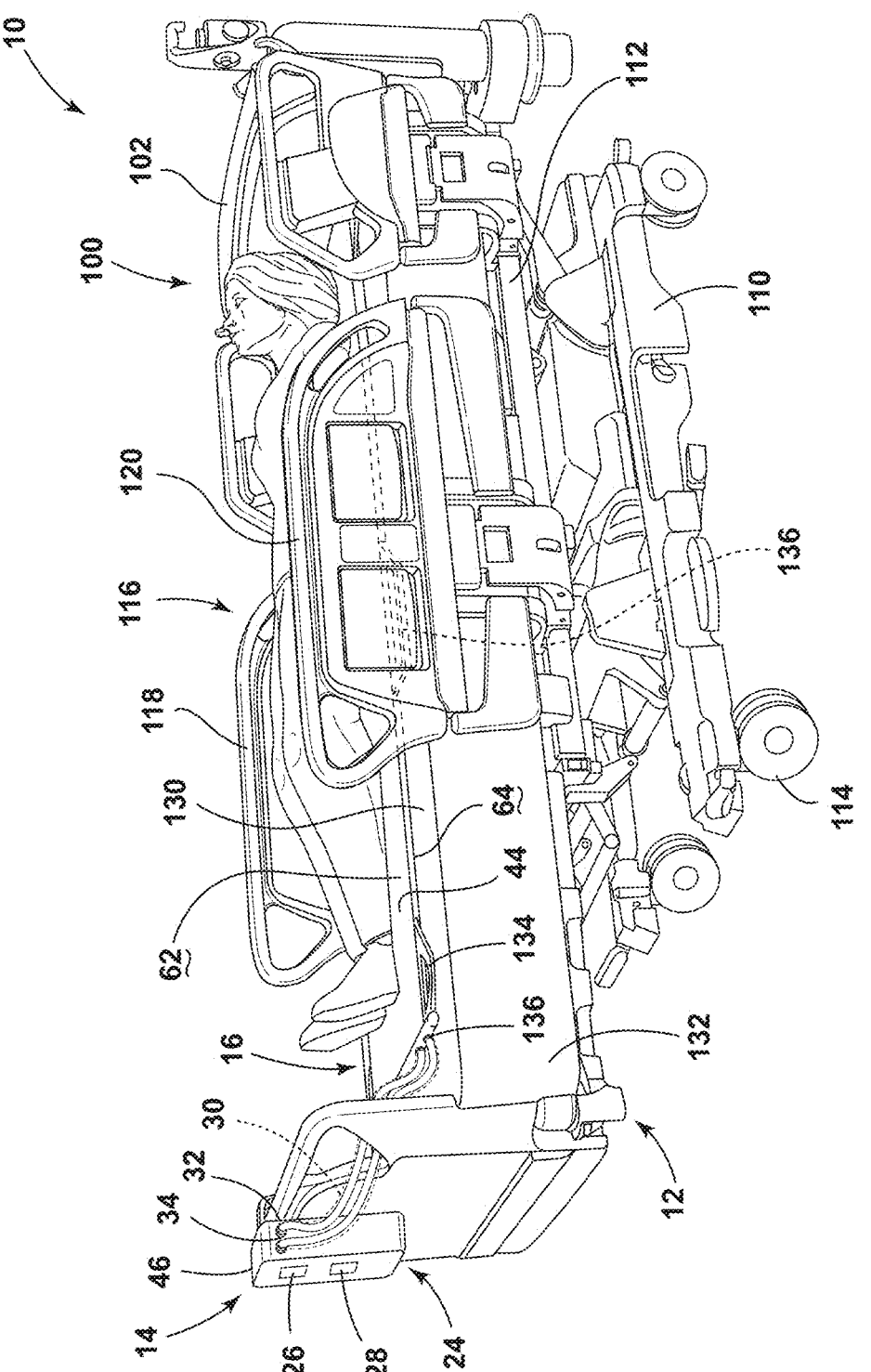
FIG. 3 is a side perspective view of a patient support system with a medical bed and a portable support surface system, according to the present disclosure.
Figures 4, 5:
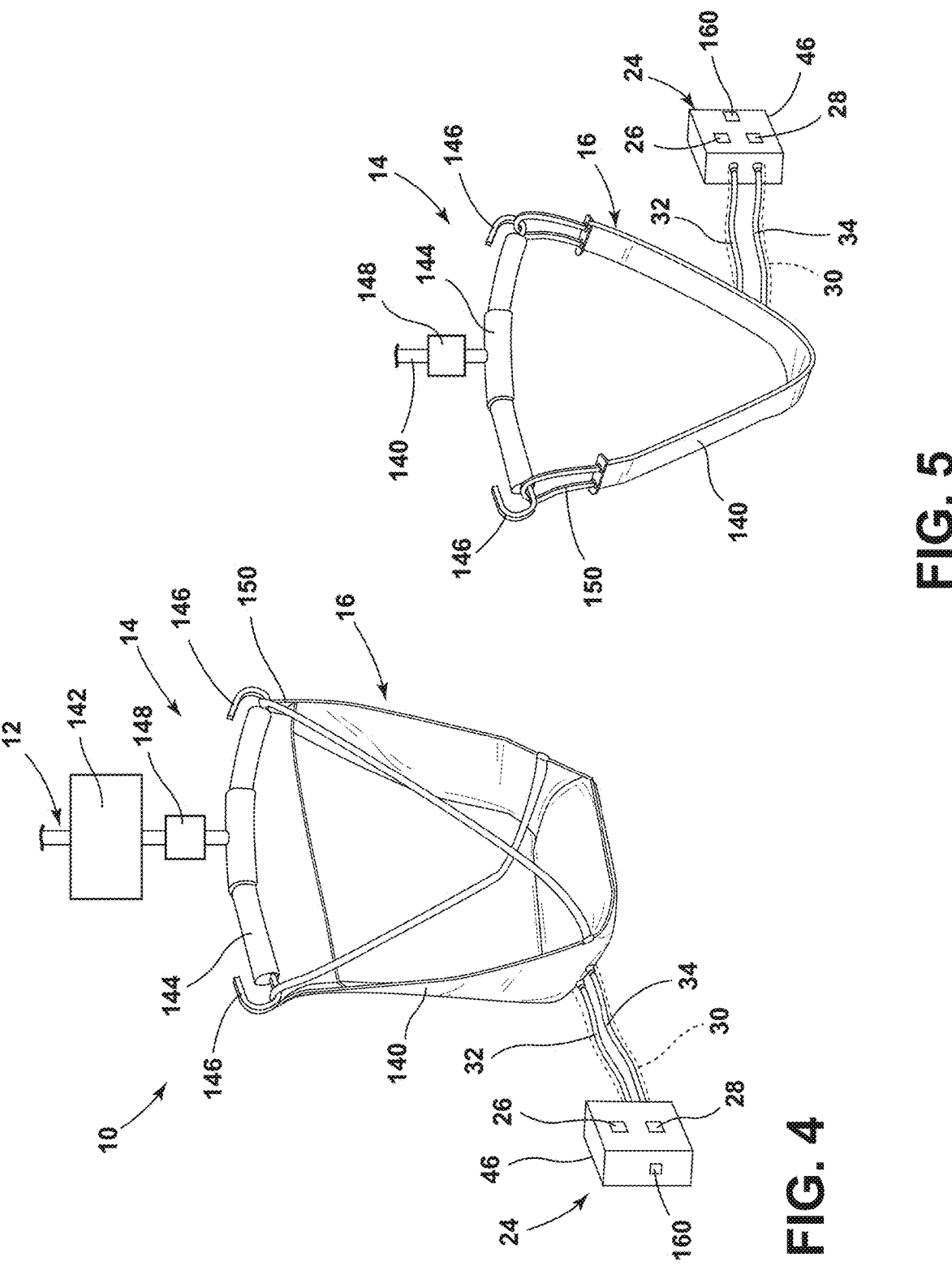
FIG. 4 is a partial side perspective view of a patient support system with a lift system and a sitting lift aid, according to the present disclosure.
FIG. 5 is a side perspective view of a patient support system with a strap lift aid, according to the present disclosure.
Figure 6:
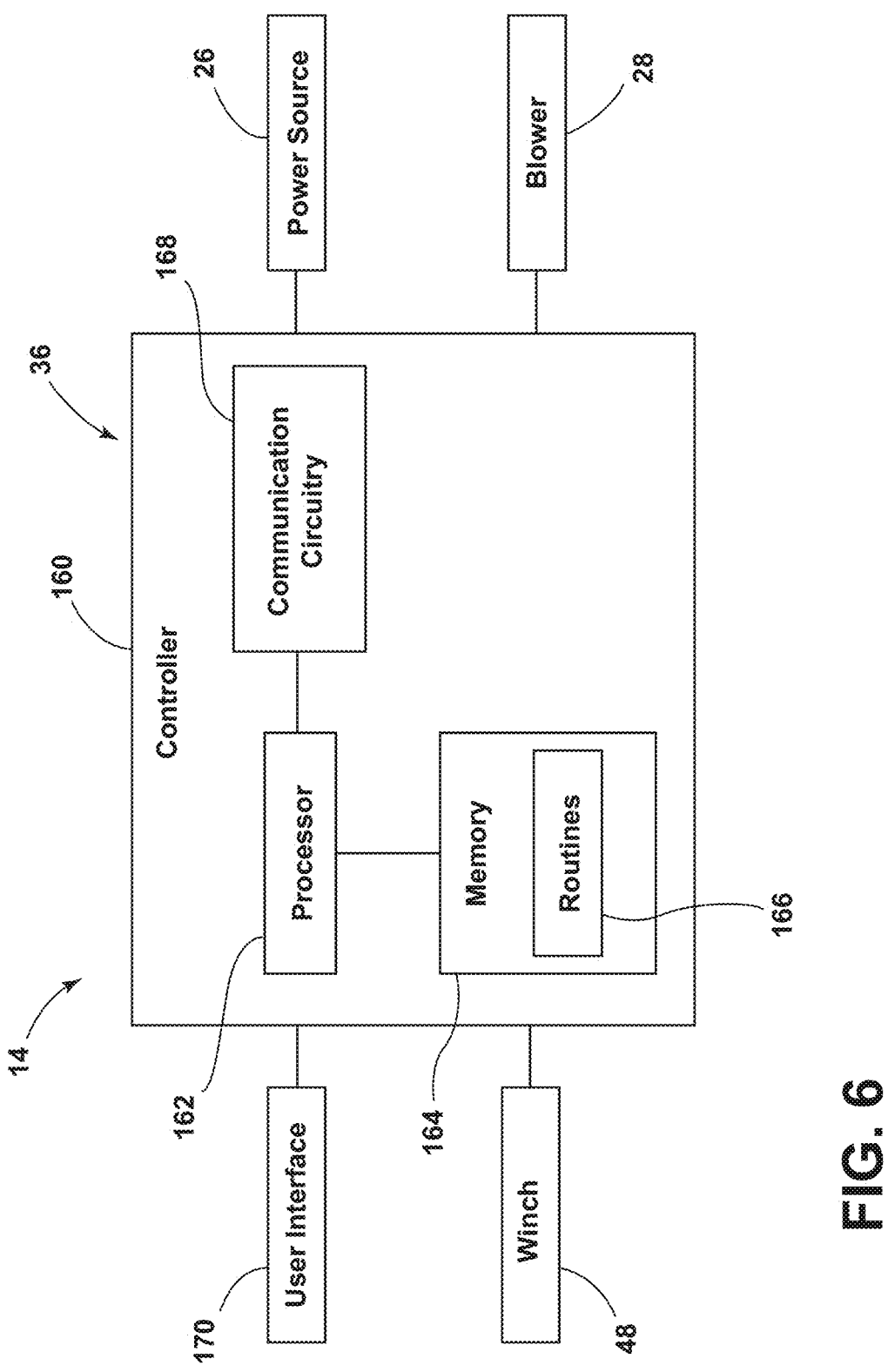
FIG. 6 is a block diagram of a support surface system including a control assembly and a surface assembly, according to the present disclosure.

Referring still to FIG. 1, as well as FIGS. 3-5, the surface assembly 16 is supported by the frame assembly 12 to hold or support the person or patient on the surface assembly 16. The surface assembly 16 may be positioned on the frame assembly 12 or may hang from the frame assembly 12, depending on the configuration of the surface assembly 16. The surface assembly 16 may be generally thin and flexible and is utilized to support the patient over an extended period of time. In this way, the surface assembly 16 may be transported with the patient to different units in a medical facility. The surface assembly 16 provides different treatments to the patient, which may be continued as the patient is transported, transferred, and positioned on the surface assembly 16.

The surface assembly 16 may be utilized on a variety of patient support apparatuses 100. The support apparatus 100 can be a medical bed 102 (FIG. 3), a lift support frame, a stretcher 104 (see FIG. 15), a surgical or operating table 106 (see FIG. 17), or other similar structures. Depending on the type of support apparatus 100, the patient may be positioned on the support apparatus 100 for an extended period of time in one place, such as a patient room or surgical suite, or for being transported about the medical facility. The surface assembly 16 is generally positioned on the support apparatus 100 below the patient. In lift configurations, the surface assembly 16 may be positioned to hang from the support apparatus 100. Additionally, the surface assembly 16 is transferred between different types of support apparatuses 100 while supporting the patient, as described further herein. In this way, the functions provided by the surface assembly 16 may be continually offered to the patient.

Referring still to FIG. 3, the medical bed 102 includes the frame assembly 12 with a base frame 110 coupled to an upper frame 112. The upper frame 112 is adjustable relative to the base frame 110 (e.g., raise, lower, tilt, etc.). Additionally, the upper frame 112 generally includes multiple segments that are independently adjustable relative to one another, allowing the upper frame 112 to articulate between various positions (e.g., an elevated head region, elevated foot region, etc.). The medical bed 102 generally includes actuation assemblies for adjusting the upper frame 112 and the segments. The base frame 110 includes wheels 114 for moving the medical bed 102 relative to an underlying floor surface. The medical bed 102 also includes siderails 116, which are generally adjustable between a raised position and a lowered position. The medical bed 102 includes at least a first siderail 118 on a first side of the upper frame 112 and a second siderail 120 on a second side of the upper frame 112.

In examples where the surface assembly 16 is disposed on the medical bed 102 or any configuration of the support apparatus 100, the surface assembly 16 is generally configured as a coverlet 130. The coverlet 130 extends across the upper frame 112 or an additional surface unit 132, such as a mattress, a mattress pad, a therapy surface unit 132 (e.g., including a pneumatic system), etc. The coverlet 130 extends from the proximate a head end of the support apparatus 100 to proximate a foot end of the support apparatus 100, which generally allows the patient to be positioned entirely on the coverlet 130. Further, the coverlet 130 generally extends a substantial portion of a width of the frame assembly 12. In certain aspects, the coverlet 130 may be between about 20 inches and 25 inches in width to support the patient and allow for movement of the siderails 116.

The coverlet 130 includes the outer covering 44 enclosing the spacer material 18 and the thermoelectric device 20. The coverlet 130 also includes or defines handles 134. As illustrated, the coverlet 130 defines four handles 134 with one at each corner of the coverlet 130. This provides grasping locations for a caregiver on each lateral side, a head end, and a foot end of the coverlet 130. Additionally, the coverlet 130 includes or defines one or more connection features 136 for coupling with the control assembly 24. The connection features 136 can be disposed in any practical location on the coverlet 130, such as the foot end, as illustrated in FIG. 3, and/or on lateral sides proximate to the siderails 116 (see FIG. 10). In certain aspects, the coverlet 130 may include multiple connection features 136 for coupling with the control assembly 24 at various locations or with various configurations of the control assembly 24. Each connection feature 136 includes the power and air connection valves 56, 58 for engaging the airflow channel 32 and the electrical connection 34.

Referring again to FIGS. 4 and 5, the support surface system 14 may be utilized to support, lift, and/or hold the patient or part of the body of the patient, such as a limb. In such examples, the surface assembly 16 is configured as a lift aid 140, which includes lifts, slings, seated slings straps, mobility ambulation aids, vests, lift sheets, such as a Repo Sheet®, and similar devices. In such examples, the lift aid 140 has increased flexibility to move, reposition, and support the patient in multiple positions.

The lift aid 140 is supported by the frame assembly 12, which, in this configuration, includes a lift system 142 with a sling bar 144 having end clips 146. The lift system 142 may be a floor-based system, which may be mobile, or may be an overhead system. Generally, the lift system 142 includes a link 148 for engaging the sling bar 144 and is configured to adjust the position of the sling bar 144 relative to the patient. The lift aid 140 includes handles 150 that are coupled to the sling bar 144 with the end clips 146. The sling bar 144 may be adjusted by the lift system 142 to pull the sling bar 144 and, consequently, the lift aid 140 to assist with lifting the patient or supporting the patient in a lifted state.

The lift aid 140 includes the outer covering 44 enclosing the spacer material 18 and the thermoelectric device 20. The lift aid 140 includes or defines one or more of the connection features 136 for coupling with the control assembly 24. The connection features 136 can be disposed in any practical location on the lift aid 140. In certain aspects, the lift aid 140 may include multiple connection features 136 for coupling with the control assembly 24 at various locations or with various configurations of the control assembly 24. In additional or alternative aspects, the lift aid 140 may form a flatter surface, similar to the coverlet 130, to be used in conjunction with a traditional lift sheet or repositioning aid. Such configurations may be advantageous for providing air assistance to more traditional repositioning processes.

With reference still to FIGS. 1 and 3-5, each configuration of the surface assembly 16 provides therapeutic benefits, such as moisture wicking and temperature regulation, including both heating and cooling. The surface assembly 16 is coupled with the control assembly 24. The airflow channel 32 and the electrical connection 34 extend from the control assembly 24 and to the surface assembly 16 to engage the connection features 136. The control assembly 24 may be selectively coupled to and disengaged from the connection features 136, which may be advantageous for transporting the support surface system 14, cleaning, etc. Additionally or alternatively, the support surface system 14 may be an integrated unit, such that the control assembly 24 is fixedly coupled to the surface assembly 16.

The airflow channel 32 and the electrical connection 34 may be disposed within the tether 30 or may be separate components extending to the surface assembly 16. The configuration with the tether 30 may be advantageous for reducing the number of lines or connections between the control assembly 24 and the surface assembly 16. The blower 26 and the power source 28 are generally disposed within the housing 46, which is advantageous for moving the control assembly 24 with the surface assembly 16 and the patient. Accordingly, the support surface system 14 may be a portable system. The control assembly 24 may also be supported by the frame assembly 12. Referring still to FIGS. 3-5, as well as FIG. 6, the support surface system 14 includes a controller 36, which may be a designated system controller 160 having a processor 162, a memory 164, and other control circuitry. Instruction or routines 166 are stored in the memory 164 and executable by the processor 162. The controller 36 may also include communication circuitry 168 configured for wired or wireless bidirectional communication.

A user interface 170 is operably coupled to the housing 46 and in communication with the controller 36. The user interface 170 may be configured as a touch screen, buttons, knobs, or dials, or include other input features for controlling the control assembly 24. The caregiver may provide an input to the user interface 170, which is communicated to the controller 160. The controller 160 then controls the blower 26 and/or the power source 28 accordingly. Through the user interface 170, the caregiver can control the treatments provided by the surface assembly 16.

In various aspects, the portable support surface system 14 also includes the winch 48. The winch 48 may be disposed in or operably coupled to the housing 46. The winch 48 may be utilized for controlling the length of the tether 30. This configuration may be advantageous for reducing excess length of the tether 30 between the housing 46 and the surface assembly 16. Further, the winch 48 may be configured to shorten the length of the tether 30 for storage. In various aspects, the winch 48 is configured to increase tension on the tether 30 to shorten the length of the tether 30. In this way, the movement of the tether 30 generally does not substantially impinge or affect the communication between the blower 26 and the surface assembly 16 or the communication between the power source 28 and the surface assembly 16. The communication between the control assembly 24 and the surface assembly 16 may remain regardless of the position relative to the winch 48.

The portable support surface system 14 can be utilized on a variety of support apparatuses 100, including the medical bed 102, the stretcher 104, and the operating table 106. In this way, the support surface system 14 may be a modular system that may be added to the support apparatus 100 and also move with the patient. Moreover, the portable support surface system 14 can be used with different support devices, such as patient lifts and repositioning aids.

With reference to FIGS. 7-15, the control assembly 24 may be integrated into the support apparatus 100, including, at least, the medical bed 102, the stretcher 104, and the operating table 106. In such examples, the support surface system 14 includes the integrated control assembly 24 and the coverlet 130. Further, in various aspects, the integrated control assembly 24 may include a first side control subassembly 180 (also referred to as the first control assembly 180) and a second side control subassembly 182 (also referred to as the second control assembly 182) for powering and controlling the coverlet 130 from each of the first and second sides of the upper frame 112. It is also contemplated that a single subassembly 180 may be included on the support apparatus 100 without departing from the teachings herein.

Figure 7:
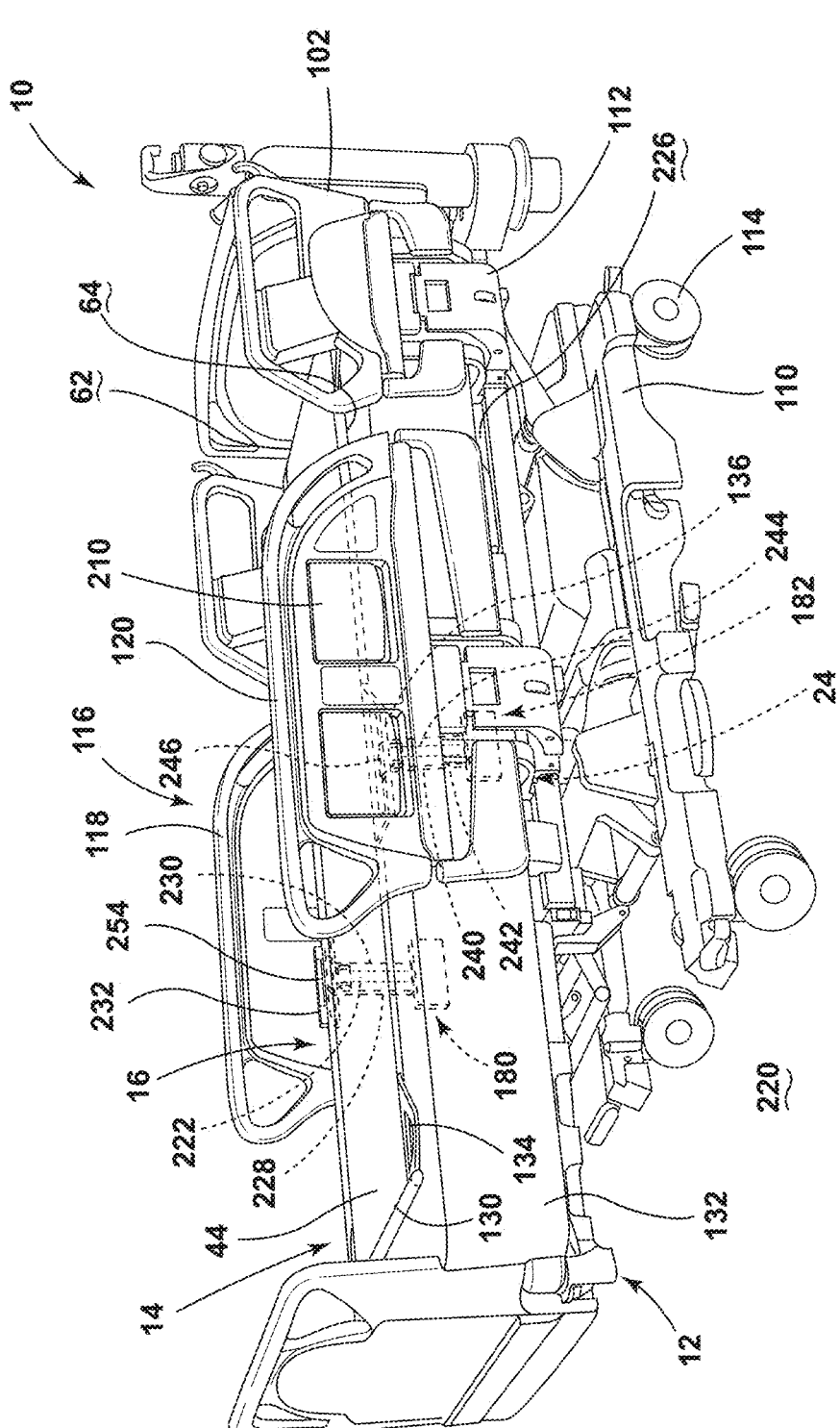
FIG. 7 is a side perspective view of a medical bed with an integrated support surface system with side assemblies, according to the present disclosure.
Figure 8:
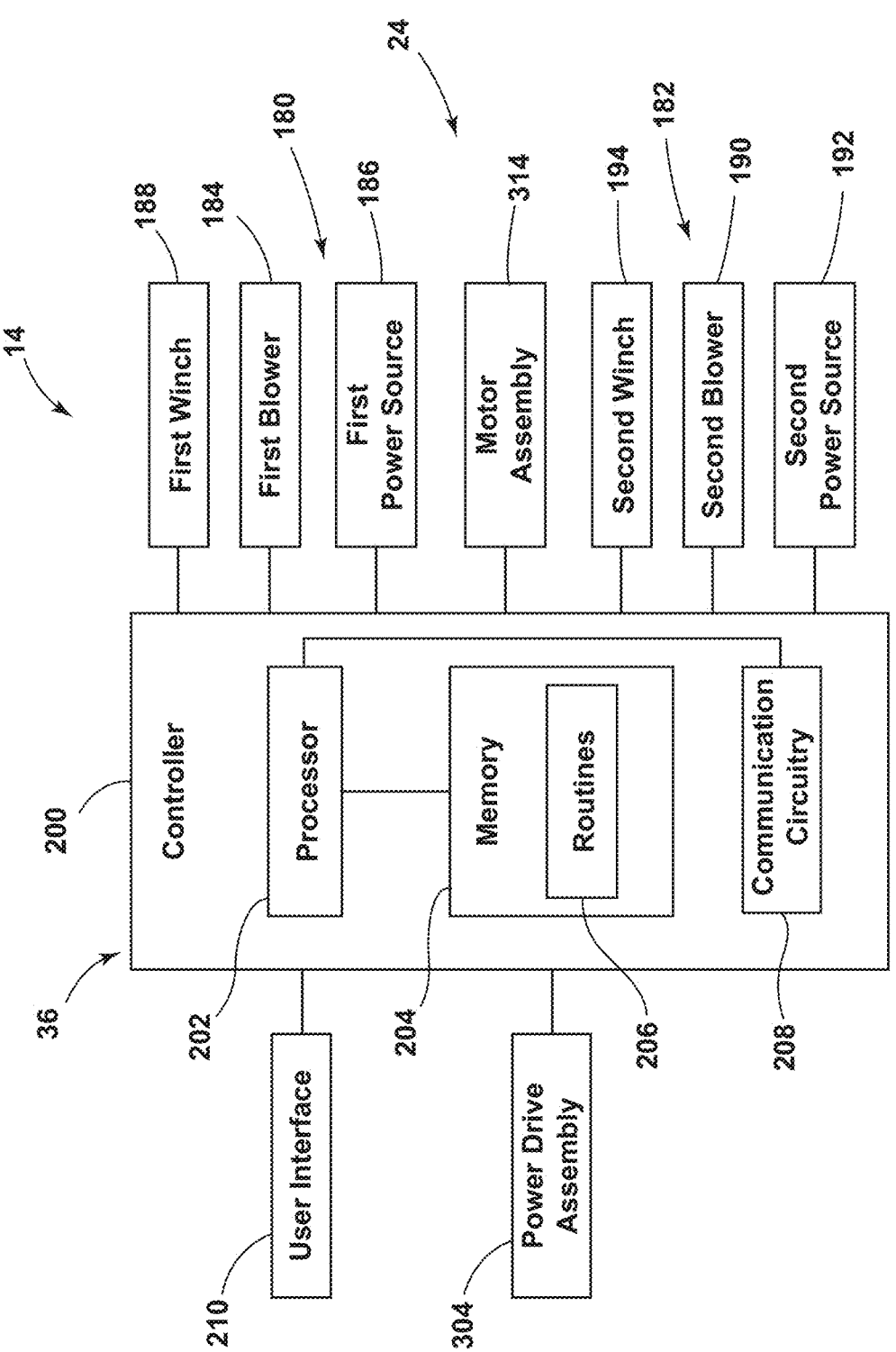
FIG. 8 is a block diagram of a patient support system with a support apparatus and a control assembly including side subassemblies, according to the present disclosure.

Referring still to FIGS. 7 and 8, the first side subassembly 180 is coupled to the first side of the frame assembly 12 and includes a first blower 184, a first power source 186, and a first winch 188. The second side subassembly 182 is coupled to the second side of the frame assembly 12 and includes a second blower 190, a second power source 192, and a second winch 194. The two side subassemblies 180, 182 include the same components and provide the same functions from opposing sides of the support apparatus 100.

The integrated control assembly 24 is generally communicatively coupled with the controller 36, which may be a controller 200 of the support apparatus 100. Accordingly, the support apparatus 100 may be used to control the control assembly 24. The controller 200 includes a processor 202, a memory 204, and other control circuitry. Instructions or routines 206 are stored in the memory 204 and executable by the processor 202. The controller 200 may also include communication circuitry 208 configured for wired or wireless bidirectional communication. The controller 200 is configured to selectively and independently control the various components of the two side subassemblies 180, 182.

The support apparatus 100 includes a user interface 210, which is typically coupled to one of the siderails 116. The user interface 210 is often configured as a graphical touch screen but may be any practicable configuration. The caregiver may utilize the user interface 210 on the siderail 120 to activate, deactivate, and control various features of the support surface system 14.

Referring still to FIGS. 7 and 8, the first side subassembly 180 is coupled to the first side of the frame assembly 12 proximate to the first siderail 118. The second side subassembly 182 is coupled to the second side of the frame assembly 12 proximate to the second siderail 120. Generally, the side subassemblies 180, 182 are coupled to or integrated into a lower surface 220 of the upper frame 112.

A first connector, belt, or tether 222 is configured to extend from the first winch 188 adjacent to the lower surface 220, through the first siderail 118 to proximate an upper surface 226 of the upper frame 112. The first tether 222 includes a first airflow channel 228 for guiding the air from the first blower 184, a first electrical connection 230 for communicating the current, and a first connector end 232 for coupling to the coverlet 130.

Similarly, a second connector, belt, or tether 240 is configured to extend from the second winch 194 adjacent to the lower surface 220, through the second siderail 120, to proximate the upper surface 226 of the upper frame 112. The second tether 240 includes a second airflow channel 242 for guiding the air from the second blower 190, a second electrical connection 244 for communicating the current, and a second connector end 246 for coupling to the coverlet 130.

The first and second tethers 222, 240 extending through the first and second siderails 118, 120 do not substantially impinge the movement of the siderails 118, 120 between the raised and lowered positions. Moreover, the first and second winches 188, 194 may adjust the first and second tethers 222, 240 to a stowed state where the tethers 222, 240 have sufficient length to allow the movement of the siderails 118, 120. Moreover, the first and second winches 188, 194 may also be automatically activated by the controller 200 based on the movement of the siderails 118, 120 to provide sufficient length for the tethers 222, 240 for coupling with the coverlet 130 and increase tension to reduce excess length.

The connector ends 232, 246 each include the power connection valve 52 and the air connection valve 54 and may be configured to clamp, insert, or otherwise engage the connection features 136 with the power and air connection valves 56, 58 of the surface assembly 16. The first and second tethers 222, 240 are operable between the stowed condition and a deployed condition via the first and second winches 188, 194, respectively. Moreover, the side subassemblies 180, 182 generally include rollers 250, which assist in guiding the movement of the tethers 222, 240 and redirecting the pull force applied by the winches 188, 194.

Figures 9, 10:
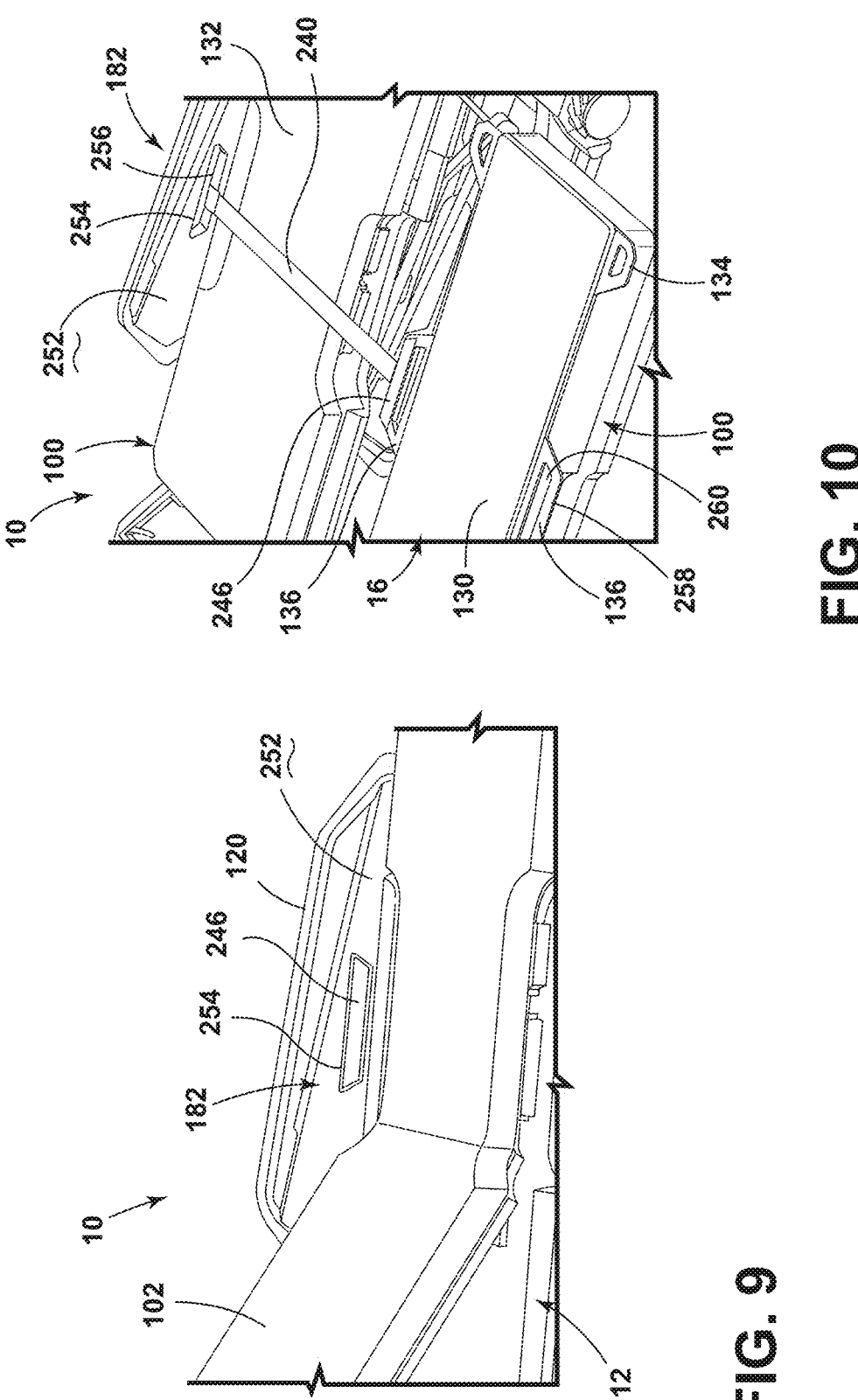
FIG. 9 is a partial side perspective view of a support apparatus including a sidewall with a recessed region for receiving a connector end of a tether of a support surface system, according to the present disclosure.
FIG. 10 is a partial side perspective view of a patient support system including two support apparatuses, each with a support surface system, and a coverlet transferable between the two support apparatuses with the support surface systems, according to the present disclosure.
Figure 11:
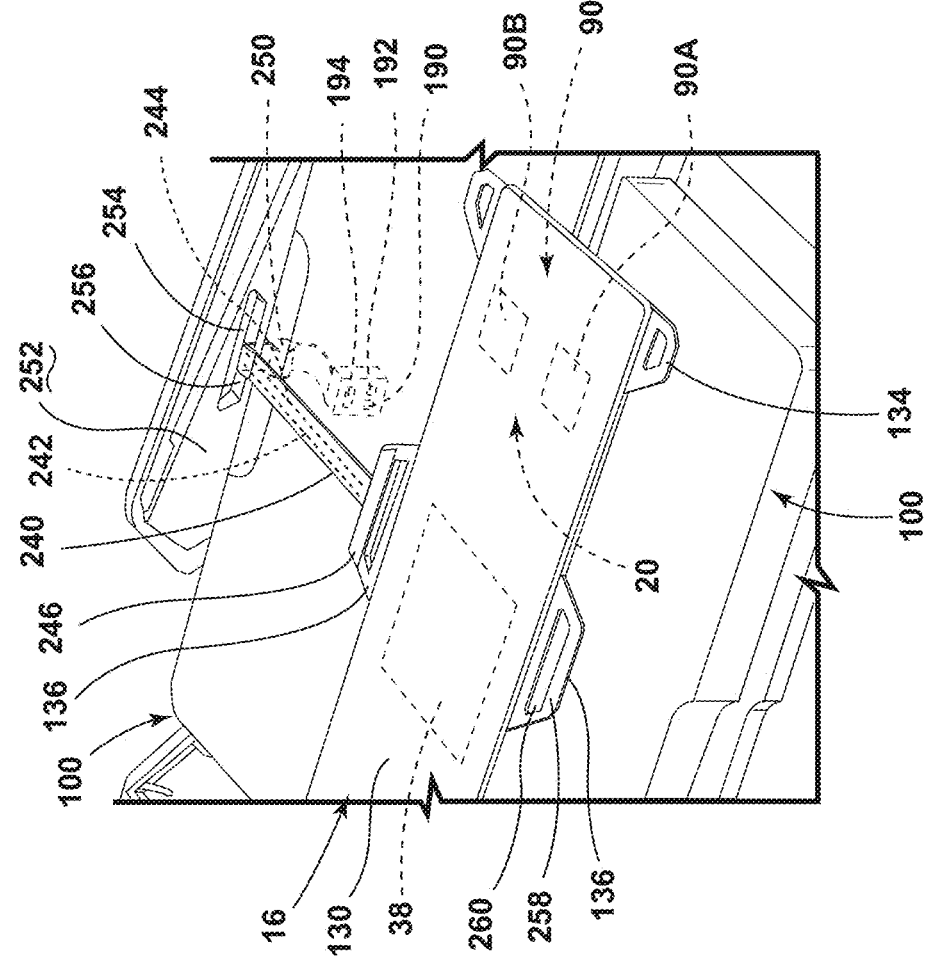
FIG. 11 is a partial side perspective view of a patient support system including two support apparatuses, each with a support surface system, and a coverlet transferable between the two support apparatuses with the support surface systems, and where the coverlet provides climate management treatment, according to the present disclosure.

The second side subassembly 182 is illustrated in FIGS. 9-11, and it is understood that the first side subassembly 180 is arranged as a mirror image and functions the same as the second side subassembly 182. The second tether 240 extends from the second winch 194, along the rollers 250, and through the second siderail 120. The second connector end 246 is disposed proximate to an inner surface 252 of the second siderail 120 and is configured to extend different distances from the second siderail 120.

The second siderail 120 defines a recessed region 254 on the inner surface 252 thereof, and a passthrough 256 for the second tether 240 is defined in the recessed region 254. In this way, the second tether 240 exits the second siderail 120 in the recessed region 254. This configuration provides proper alignment for the stowed condition. In the stowed condition, the second connector end 246 is disposed within the recessed region 254 and generally fills the recessed region 254. The second connector end 246 may be substantially flush with the inner surface 252 to minimize space utilized by the support surface system 14 when stowed. The caregiver may adjust the connector end 246 out of the recessed region 254 for use. The siderail 120 may define a notch, a button, or other feature that allows the caregiver to remove the connector end 50 from the recessed region 254. It is understood that the first siderail 118 is similarly configured to receive the first connector end 232.

The caregiver is configured to adjust the second tether 240 to the deployed condition, extending the length of the second tether 240 and moving the second connector end 246 farther from the second siderail 120. The second tether 240 is configured to extend across the upper frame 112 and beyond the second side. This configuration is advantageous for coupling with the coverlet 130 on an adjacent support apparatus 100 as assisting in patient transfer as described herein. Once deployed, the second winch 194 can be activated to increase the tension of the second tether 240 and pull the second tether 240 to a shorter length and/or to pull the second tether 240 to the stowed condition. During the pulling process, the rollers 250 are configured to redirect the pull force vector toward the second siderail 120 to pull the second tether 240 through the second siderail 120 and stow the excess length of the second tether 240 below the upper frame 112.

Figures 12A, 12B:
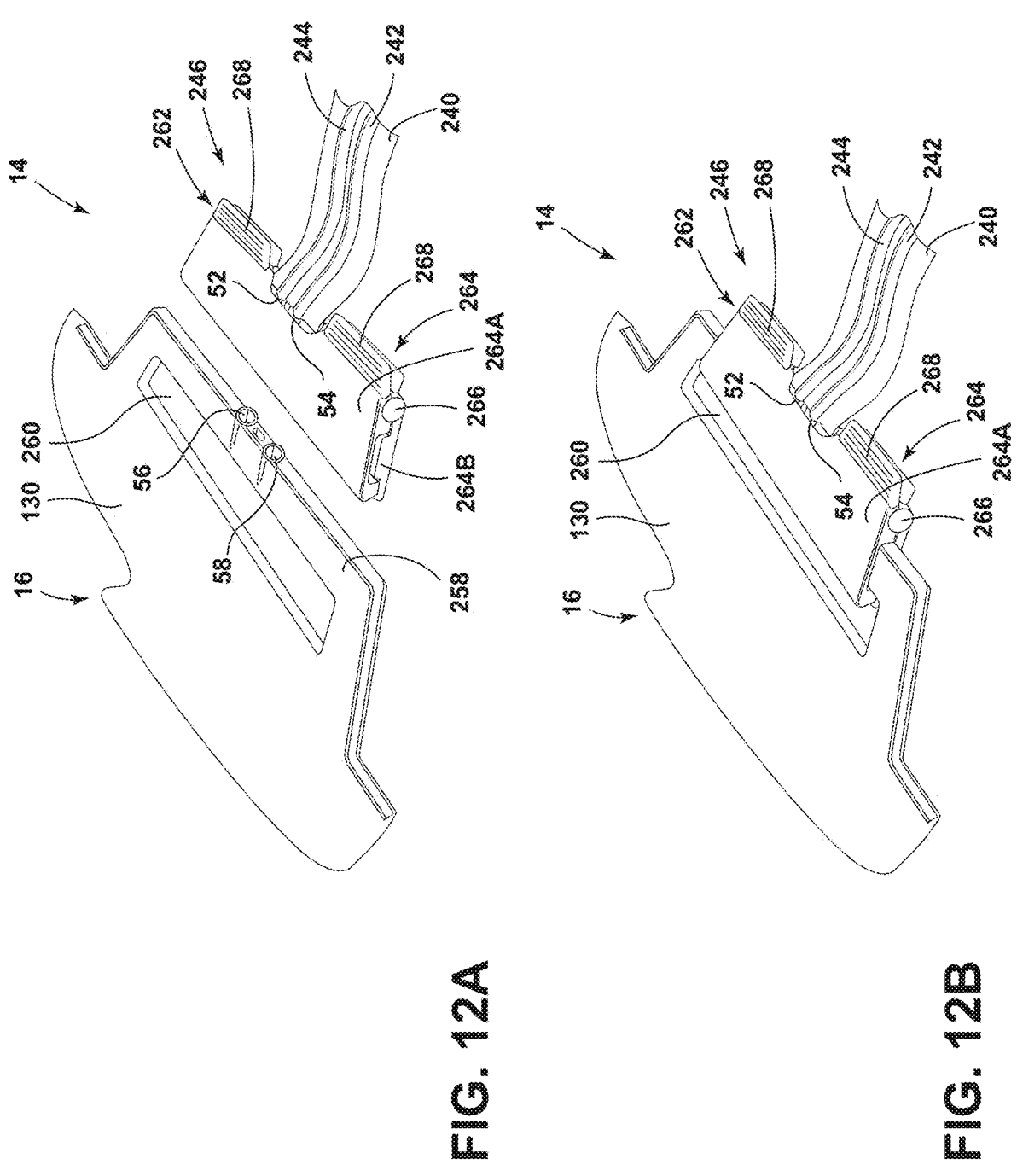
FIG. 12A is a partial side perspective view of a support surface system with a connector end for engaging a connection feature of a surface assembly, according to the present disclosure.
FIG. 12B is a partial side perspective view of a support surface system with a connector end engaging a connection feature of a surface assembly to provide air and power, according to the present disclosure.
Figure 13:
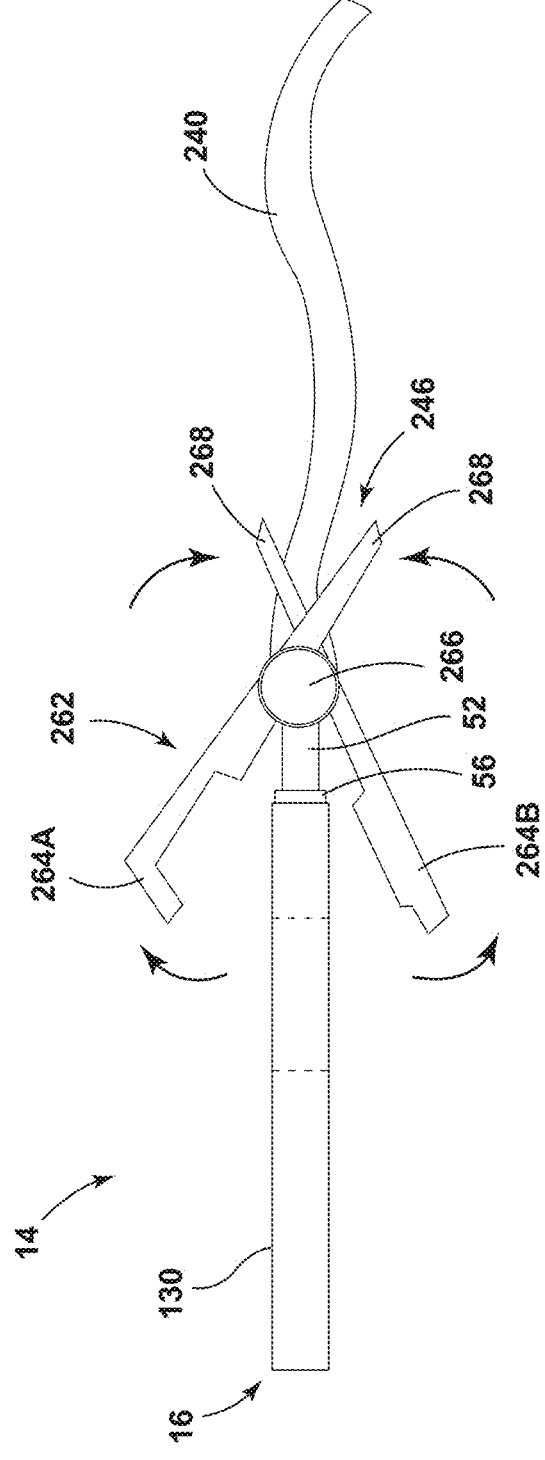
FIG. 13 is a partial schematic, cross-sectional view of a support surface system with a connector end of a tether engaging a connection feature of a surface assembly, according to the present disclosure.

Referring still to FIG. 11, as well as to FIGS. 12A-13, the coverlet 130 includes two connection features 136 on opposite sides thereof. Generally, the two connection features 136 are configured to be disposed adjacent to the siderails 118, 120, respectively, and have similar constructions to allow selective engagement of either connector end 232, 246. The connection features 136 include an extension 258 and define apertures 260. The apertures 260 may be advantageous for securely coupling the connector ends 232, 246 to the connection features 136. Further, the extension 258 may be advantageous for positioning the power connection valve 52, the air connection valve 58, the re-directing valve 60, and/or other connection components in a location to the side of the patient. In such examples, the patient is not substantially supported on the connection features 136, which may reduce pressure felt by the patient and which could cause pressure injuries.

The second connector end 246 is illustrated with one of the connection features 136 on the coverlet 130. It is contemplated that the first connector end 232 and each connection feature 136 are similarly constructed and operate in a similar manner as described with respect to the second connector end 246 and the illustrated connection feature 136, respectively. The extension 258 of the connection feature 136 includes or defines the power connection valve 56 and the air connection valve 58. The second connector end 246 includes the mating power connection valve 52 and the mating air connection valve 54. In the illustrated configuration, the second connector end 246 is configured as a clamp assembly 262 having clamps 264A, 264B (which may be referred to collectively as the clamps 264) coupled via a hinge 266. The clamp assembly 262 also includes engagement handles 268 for adjusting the clamps 264 relative to one another. In a non-limiting example, the clamp assembly 262 may be constructed of resin or as a cast metal assembly.

The hinge 266 is generally a spring-loaded hinge, which biases the clamps 264 to a closed state. The caregiver is configured to press or squeeze the engagement handles 268 toward one another, moving the clamps 264 to an opened state against the biasing force. The caregiver can then engage the power and air connection valves 56, 58 of the connection feature 136 on the coverlet 130 with the power and air connection valves 52, 54, which are between the clamps 264A, 264B adjacent to the hinge 266. The caregiver may then release the engagement handles 268, allowing the clamps 264 to close around the extension 258. In various aspects, the first clamp 264A includes a first mating feature, such as a recess, and the second clamp 264 includes a second mating feature, such as a protrusion, which assists in locking the clamp assembly 262 to the extension 258 when in the closed state. To disengage the clamp assembly 262, the caregiver can again engage the engagement handles 268 to adjust the clamps 264 to the opened state. The caregiver may then disconnect the connection valves 52, 54, 56, 58, respectively.

With reference to FIGS. 14A-14E, the coverlet 130 may have a variety of configurations. While described with respect to the coverlet 130, the structure and function may also be included in any configuration of the surface assembly 16 without departing from the teachings herein. The coverlet 130 may be used to transfer the patient between support apparatuses 100, provide temperature regulation (i.e., heating and/or cooling), provide microclimate management, or combinations thereof.

Figures 14A, 14B:
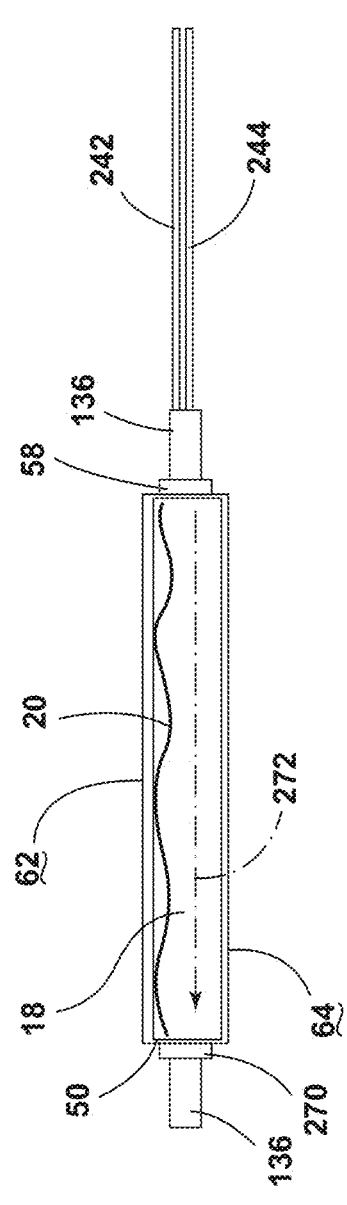
FIG. 14A is a partial schematic, cross-sectional view of a support surface system with a tether engaging a surface assembly for assisting with patient transfer between support apparatuses, according to the present disclosure.
FIG. 14B is a partial schematic, cross-sectional view of a support surface system with a tether engaging a surface assembly for assisting with patient transfer and providing heating and microclimate management, according to the present disclosure.

Referring to FIG. 14A and with continued reference to the second side subassembly 182 as an example, the second tether 240 is configured to engage the connection feature 136 on the coverlet 130. The coverlet 130 may be utilized primarily for transferring the patient while providing comfort or support to the patient. In such examples, the coverlet 130 includes the outer covering 44 including the top surface 62 and the bottom surface 64. The spacer material 18, which is generally the foam material, is disposed within the outer covering 44. The bottom surface 64 has a texture that allows for side-to-side transfer while resisting head-to-foot movement. Accordingly, the bottom surface 64 has frictional properties that are less than the top surface 62 to promote the sliding transfer of the patient and the coverlet 130 together, while reducing movement of the patient relative to the coverlet 130.

With reference to FIG. 14B, the coverlet 130 may be configured to provide thermoelectric heat and microclimate management. In such examples, the second tether 240 provides the airflow and the power to the coverlet 130. The coverlet 130 includes the outer covering 44, which defines vents 270 and the connection features 136. The coverlet 130 also includes the spacer material 18 and the thermoelectric device 20 in the spacer material 18. The vents 270 may be arranged in a variety of locations to provide an airflow through the spacer material 18. The spacer material 18 defines air channels 272 that are in fluid communication with the air connection valve 58 and the vents 270 to provide the airflow through the coverlet 130. The thermoelectric device 20 is disposed proximate to the top surface 62 to provide the heat to the patient. In addition to the heating and microclimate management, the bottom surface 64 also has decreased frictional properties to promote the sliding transfer of the patient.

Figure 14C:
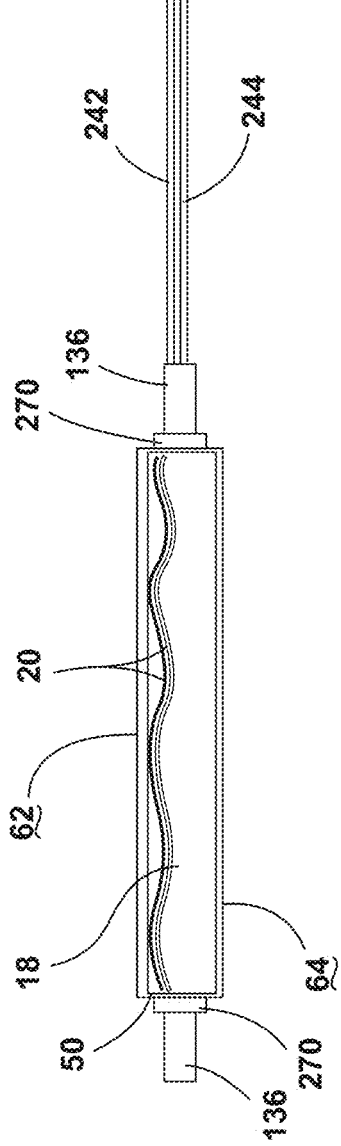
FIG. 14C is a partial schematic, cross-sectional view of a support surface system with a tether engaging a surface assembly for assisting with patient transfer and providing heating, cooling, and microclimate management, according to the present disclosure.

With reference to FIG. 14C, the coverlet 130 may be configured to provide thermoelectric heating and cooling, as well as microclimate management. Similar to the coverlet 130 described with respect to FIG. 14B, the coverlet 130 illustrated in FIG. 14C includes the outer covering 44 defining the vents 270 and the connection features 136, the spacer material 18, and the thermoelectric device 20 in the spacer material 18. The power is provided through the second tether 240 to the thermoelectric device 20 to direct the current in specific directions to provide the heating and cooling effects, respectively. The air is provided through the second tether 240 and through the air channels 272 in the spacer material 18.

Figure 14D:
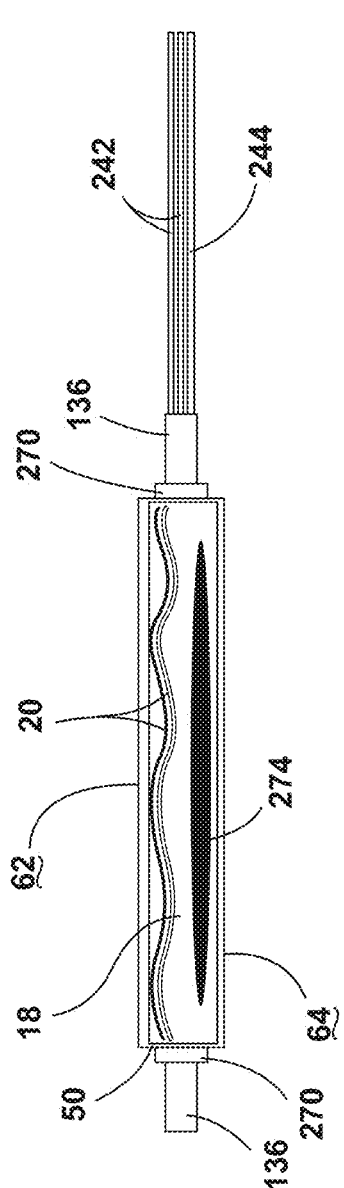
FIG. 14D is a partial schematic, cross-sectional view of a support surface system including an air bladder for assisting with patient transfer and providing heating, cooling, and microclimate management, according to the present disclosure.

With reference to FIG. 14D, the coverlet 130 may be configured to provide thermoelectric heating and cooling and microclimate management, similar to the coverlet 130 described with respect to FIG. 14C, and also include an air bladder 274 to assist with transferring the patient. The power can be provided through the second tether 240 to direct the current in different directions through the thermoelectric device 20 to provide the heating and cooling. The second tether 240 also provides the air to the air channels 272 and/or the air bladder 274. In various examples, two airflow channels 242 may be provided in the second tether 240 to separately direct air through the spacer material 18 and to the air bladder 274. Additionally or alternatively, the re-directing valve 60 may divert the airflow from the spacer material 18 to the air bladder 274 to assist with the transfer and again divert the airflow back to the spacer material 18 after the transfer.

The air bladder 274 is configured to adjust to a deployed or inflated state, providing a raised or "hover" effect to the coverlet 130. The inflated air bladder 274 may decrease the surface area of the coverlet 130 engaging the support apparatus 100, reducing a frictional engagement therebetween and promoting the sliding transfer. Upon completion of the patient transfer, the air bladder 274 may be adjusted to a non-deployed or deflated state, allowing the air from the air bladder 274 to be expelled through the vents 270.

In additional or alternative aspects, the air bladder 274 may be operated independently of the support surface system 14. In such examples, an additional or auxiliary air source may be utilized for inflating and deflating the air bladder 274. For example, a traditional blower may be coupled to the coverlet 130 for inflating the transfer bladder 274 during the transfer process and then disconnected when the transfer process is complete.

Figure 14E:
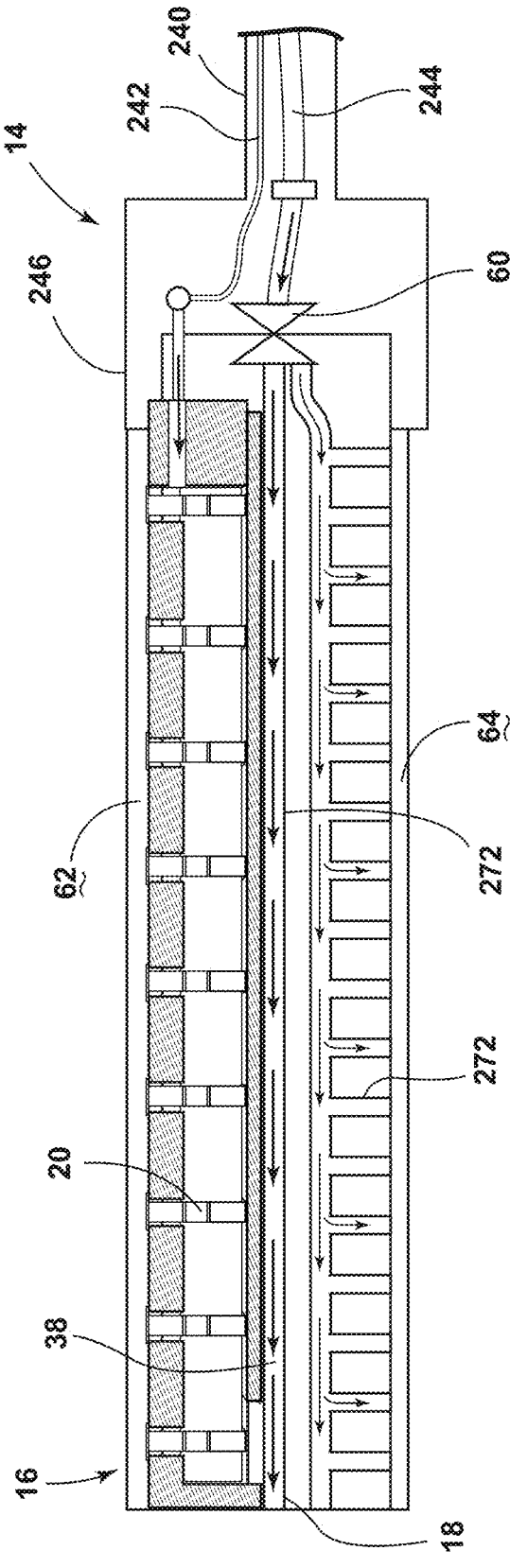
FIG. 14E is a partial schematic, cross-sectional view of a surface assembly of a support surface system including air channels for assisting with patient transfer and providing heating, cooling, and microclimate management, according to the present disclosure.

With reference to FIG. 14E, the support surface system 14 is configured to direct the air through the coverlet 130 in multiple directions along multiple airflow paths to assist with the transfer. The coverlet 130 may include air channels 272 extending horizontally through the spacer material 18, forming a first airflow path, and air channels 272 extending vertically through the spacer material 18, forming a second airflow path. The re-directing valve 60, which may be included in the coverlet 130 or the second tether 240, may redirect the air between the MCM layer 38 and the bottom surface 64 of the outer covering 44 through the vertically oriented air channels 272.

The re-directing valve 60 is configured to redirect the air from the blower 190 to be directed downwards, towards the upper frame 112 or additional surface unit 132. The air blowing through the bottom surface 64 produces the "hover" effect for the coverlet 130, allowing for easier movement (e.g., utilizing less manual force by the caregiver) of the coverlet 130 relative to the support apparatus 100 while supporting the patient. In various aspects, the re-directing valve 60 may be configured to temporarily block the airflow to the surface assembly 16, building pressure within the second tether 240 and/or the control assembly 24. Upon opening the fluid communication for generating the "hover" effect, the increased pressure may result in a more powerful airflow through the bottom surface 64, to increase the strength of the "hover" effect. The first side subassembly 180 generally operates in a similar manner when coupled to the coverlet 130.

Typically, when providing the "hover" effect as illustrated in FIGS. 14D and 14E, the air is not flowing through the spacer material 18. Accordingly, at least the moisture-wicking treatment may be temporarily paused during the patient transfer using the "hover" effect. The temperature regulation may continue or be paused during the patient transfer. It is contemplated that in certain aspects, the airflow may generate the "hover" effect and provide the moisture-wicking treatment concurrently without departing from the teachings herein.

The direction of the airflow and the control of the re-directing valve 60 may be controlled by the controller 200 of the support apparatus 100 and/or the caregiver through an input in a user interface. Accordingly, the caregiver may trigger the redirection of the airflow from the MCM layer 38 to the bottom surface 64 and back to the MCM layer 38. Alternatively, the controller 200 may automatically redirect the airflow from the MCM layer 38 to the bottom surface 64 for a predefined period of time upon engagement with the connector end 232, 246 of one of the tethers 222, 240.

Referring again to FIGS. 15-17, the support surface system 14 is configured to provide treatment to the patient and assist in patient transfer between different support apparatuses 100. In this way, the support surface system 14 is utilized for transferring the patient between support apparatuses 100 along with the coverlet 130. This is advantageous for continuing to provide the various treatments while the patient is positioned on the surface assembly 16 for an extended period with minimal or no interruptions in treatment.

The different support apparatuses 100 may each include the support surface system 14. The support surface system 14 in the medical bed 102, the stretcher 104, and the operating table 106 may be substantially similar. The stretcher 104 includes the frame assembly 12 with a base frame 278 and an upper frame 280 coupled to the base frame 278. The upper frame 280 generally forms a deck 294 for supporting a patient thereon, while the base frame 278 includes a pedestal 282 and a base support 284. The pedestal 282 extends between the upper frame 280 and the base support 284. The pedestal 282 is generally centrally located relative to the upper frame 280 though it is contemplated that more than one pedestal 282 may be included in the stretcher 104. Support legs 286 are coupled to and extend from the base support 284 and include wheels or rollers 288, allowing the stretcher 104 to be transportable around the medical facility. Other configurations of the stretcher 104 may be utilized without departing from the teachings herein.

The upper frame 280 is movable relative to the pedestal 282. The upper frame 280 may tilt, rotate, lift, lower, or otherwise move relative to the pedestal 282. Additionally, the upper frame 280 may include multiple segments that may be independently movable relative to one another, allowing movement of a certain portion of the upper frame 280 separately. The upper frame 280 is configured to support the additional surface unit 132, the coverlet 130, and the patient. The stretcher 104 also includes first and second siderails 290, 292 on opposing sides of the upper frame 280.

The support surface system 14 utilized with the stretcher 104 includes the control assembly 24 with the two side subassemblies 180, 182. The first side subassembly 180 is coupled to the first side of the upper frame 280 with the first tether 222 extending through the first siderail 290. The second side subassembly 182 is coupled to the second side of the upper frame 280 with the second tether 240 extending through the second siderail 292.

Figure 15:
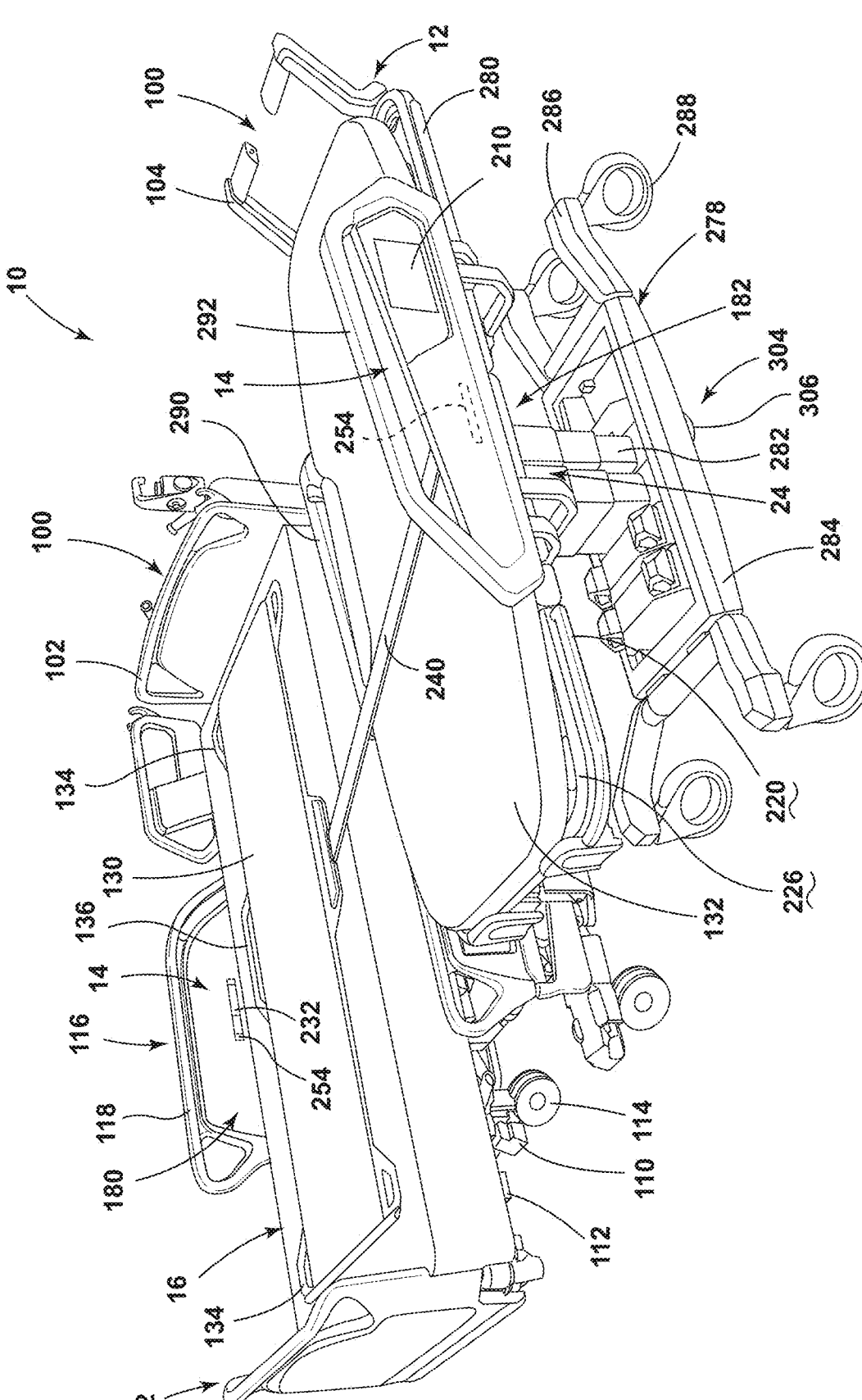
FIG. 15 is a side perspective view of a patient support system including multiple support apparatuses, each with a support surface system, and a coverlet transferable between the support apparatuses with the support surface systems, and where the coverlet is on a medical bed, according to the present disclosure.
Figure 16:
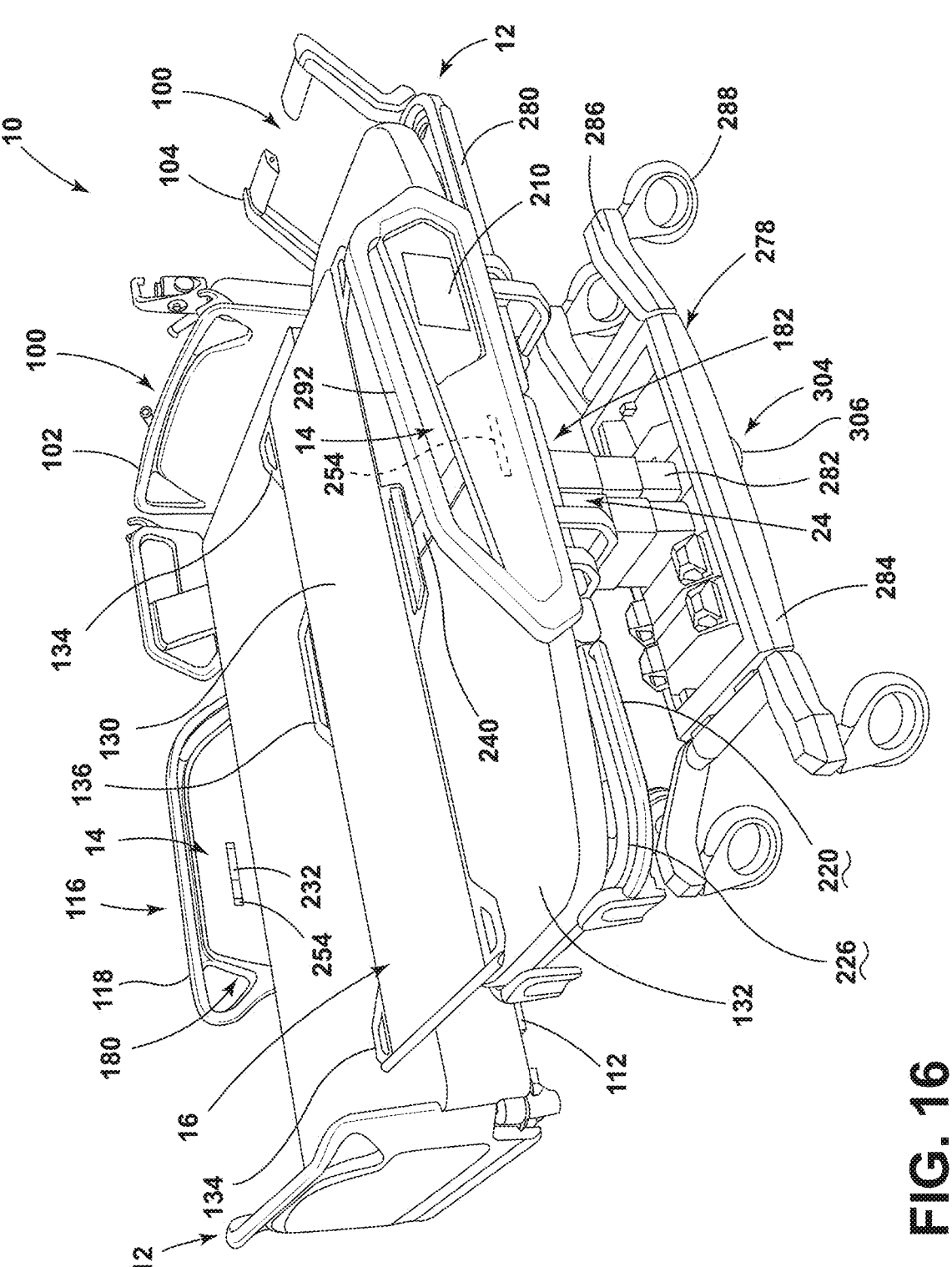
FIG. 16 is a side perspective view of a patient support system including multiple support apparatuses, each with a support surface system, and a coverlet transferable between the support apparatuses with the support surface systems, and where the coverlet is being moved from a medical bed to a stretcher, according to the present disclosure.
Figure 17:
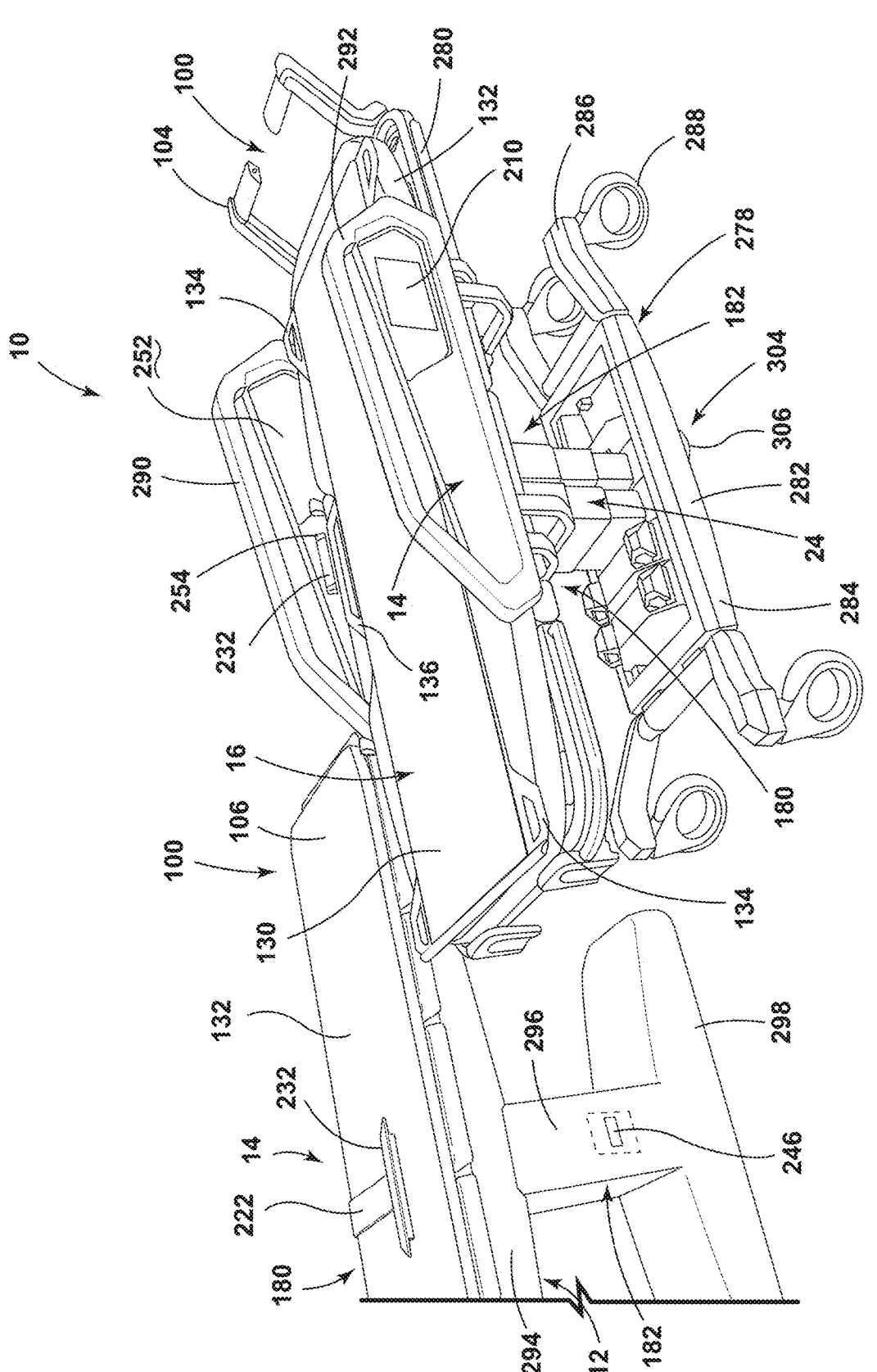
FIG. 17 is a side perspective view of a patient support system including multiple support apparatuses, each with a support surface system, and a coverlet transferable between the support apparatuses illustrated as a stretcher and an operating table, according to the present disclosure.

Referring still to FIGS. 15-17, the operating table 106 includes the frame assembly 12 having a deck 294 for supporting the patient thereon, a pedestal 296, and a base support 298. The pedestal 296 extends between the deck 294 and the base support 298. The pedestal 296 is generally centrally located relative to the deck 294; however, it is contemplated that more than one pedestal 296 may extend between the deck 294 and the base support 298. The base support 298 generally includes rollers, allowing the operating table 106 to be transportable around the surgical suite or otherwise transportable about the medical facility.

The deck 294 is generally movable relative to the pedestal 296. The deck 294 may tilt, rotate, or otherwise move relative to the pedestal 296. Additionally, the deck 294 may include multiple segments that may be independently movable relative to one another allowing movement of a certain portion of the deck 294 separately. The deck 294 generally has a modular construction that allows access to items positioned on the deck 294 from an area under the deck 294. This configuration of the deck 294 is advantageous for providing connections to items on the deck 294 while stowing the connections (e.g., cords, wiring, tubing, etc.) in a location that does not substantially interfere with the caregiver or the surgical procedure.

Unlike the medical bed 102 and the stretcher 104, the operating table 106 generally does not include siderails. Accordingly, the control assembly 24 is integrated into the frame assembly 12 and the tethers 222, 240 extend toward the surface assembly 16 along an outer edge of the deck 294. The control assembly 24 may be integrated into the pedestal 296, the base support 284, 298, or the deck 294. The connector ends 232, 246 of the tethers 222, 240 may abut an outer surface of the frame assembly 12 when stowed, or the frame assembly 12 may define the recessed regions for receiving the connector ends 232, 246. A user interface for the operating table 106 may be disposed in any practicable location and can be used to control the support surface assembly 16. Additionally or alternatively, the operating table 106 may include the system-designated user interface 170 for controlling the support surface system 14.

Referring still to FIGS. 15-17, the support surface system 14 can be used to transfer the patient between different support apparatuses 100. For example, the patient may be in the patient room and supported on the medical bed 102. While on the medical bed 102, the patient can be positioned on the coverlet 130, which is coupled with the first side subassembly 180. The first side subassembly 180 provides air and power to the MCM layer 38 and the thermoelectric device 20, respectively. In this way, moisture-wicking and temperature-regulating treatments may be provided for the patient.

When the patient is to be moved, for example to a surgical suite, the stretcher 104 is moved proximate to the medical bed 102. The first side subassembly 180 of the medical bed 102 may be disengaged from the coverlet 130. The caregiver may move the second tether 240 from the stretcher 104 to the deployed state, crossing the upper frame 112 of the stretcher 104 to engage the coverlet 130 still positioned on the medical bed 102 with the patient. Accordingly, the second side subassembly 182 of the stretcher 104 provides air and power to the MCM layer 38 and the thermoelectric device 20 to the coverlet 130.

The caregiver is configured to align the support apparatuses 100 adjacent to one another to provide a more even surface for transferring the patient from one support apparatus 100 to the adjacent support apparatus 100. As illustrated in FIGS. 13 and 14, the stretcher 104 and the medical bed 102 are adjusted to provide flat surfaces at a generally similar height to provide a continuous surface for sliding the patient and the coverlet 130.

According to various aspects, at least some of the support apparatuses 100, such as the medical bed 102 and the stretcher 104, may include a power drive assembly 304. The power drive assembly 304 may assist with driving movement of the support apparatuses 100. The power drive assembly 304 may also assist in aligning the support apparatuses 100 adjacent to one another.

The power drive assembly 304 generally includes a power drive wheel 306 that is operable between a retracted position, spaced from the floor surface, and a deployed position to engage the floor surface. The power drive assembly 304 also includes a motor operably coupled with the power drive wheel 306 for causing rotation of the power drive wheel 306 in a power drive mode. The motor is generally a variable-speed, bidirectional motor that has a rotatable output shaft. In various aspects, a selectively engageable clutch selectively couples the motor to the drive wheel 306 when the clutch is engaged. In certain aspects, the clutch may include a drive pulley coupled to the output shaft of the motor and an axle of the drive wheel 306. In such examples, a belt extends between the drive pulley and a follower or driven pulley operably coupled with the drive wheel 306. An idler is operably coupled to the body and an actuator. The idler is adjusted by the actuator relative to the belt to be either spaced from the belt or pressed into the belt to put the belt under tension to transform rotation from the motor to the drive wheel 306 and propel the support apparatus 100.

According to various aspects, the power drive assembly 304 is rotatable to propel the support apparatus 100 in different directions. In such examples, the power drive assembly 304 is operable between a first direction, with the power drive wheel 306 oriented between the head end and the foot end to propel the support apparatus 100 forward, and a second direction, with the power drive wheel 306 oriented between the first side and the second side to propel the support apparatus 100 to the side or laterally. The power drive wheel 306 may also be oriented between the first and second directions to propel the support apparatus 100 at an angle, both slightly forward/back and slightly to the side. The power drive wheel 306 may be lowered and rotated to assist in guiding one support apparatus 100 adjacent to another for the patient transfer.

Referring still to FIGS. 15-17, once the medical bed 102 and the stretcher 104 are adjacent to and aligned with one another, the caregiver can activate the second winch 194 of the stretcher 104 via the user interface 210 on the stretcher 104. The caregiver can also change the direction of the airflow. The change in airflow direction can be done through the interface 210 or through manual actuation of the re-directing valve 60, such as with a button or switch. The airflow is directed downwards to provide the "hover" effect and/or to fill the transport bladder 274. The first winch 188 of the stretcher 104 then retracts to apply a pulling force on the coverlet 130 to pull the coverlet 130 toward the stretcher 104. The caregiver can utilize the handles 134 to assist with moving and guiding the coverlet 130 to the stretcher 104.

When the coverlet 130 is fully disposed on the upper frame 280 of the stretcher 104, the airflow can return to being directed through the spacer material 18 to provide the moisture-wicking treatment. In this way, the patient can receive the moisture-wicking treatment and/or the temperature regulation treatment, including heating and/or cooling while being transported.

The patient is then transported to the surgical suite while receiving climate management treatment. The stretcher 104 is moved adjacent to the operating table 106 and the process begins again to transfer the patient to the surgical table 106. The first side subassembly 180 of the operating table 106 is adjusted for the first tether 222 to extend across the deck 294 and engage the coverlet 130 on the stretcher 104. This is on an opposing side from where the second tether 240 of the stretcher 104 engages the coverlet 130. The second tether 240 from the stretcher 104 can be disengaged from the coverlet 130. The first tether 222 from the operating table 106 can then provide the power and the air to the coverlet 130. The caregiver can activate the first winch 188 of the operating table 106 and switch the airflow to provide the "hover" effect. The caregiver can then assist in guiding the coverlet 130 and the patient to the operating table 106 with the handles 134 as the first winch 188 pulls the tether 222 of the operating table 106.

Figure 18:
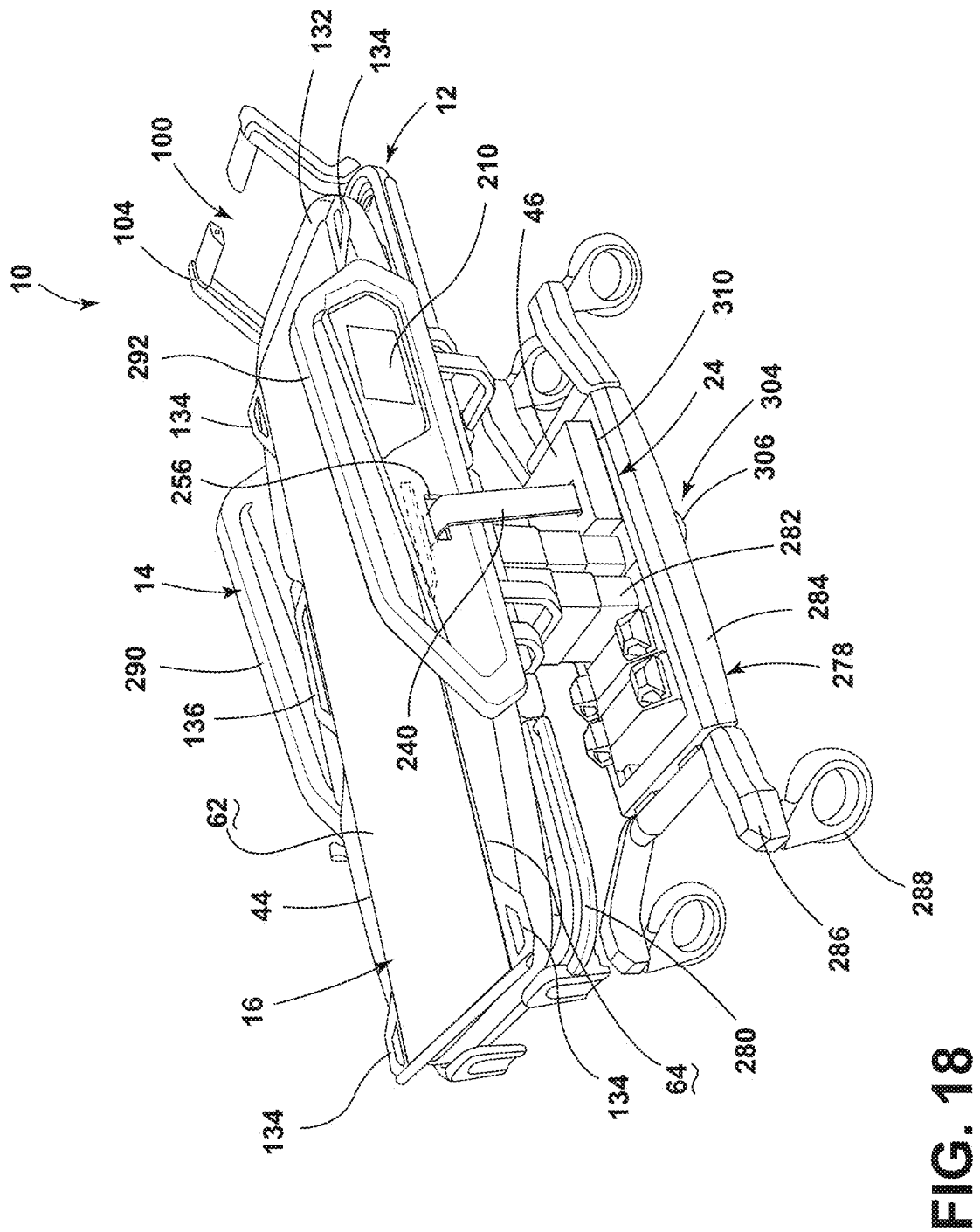
FIG. 18 is a side perspective view of a support apparatus with a modular support surface system, according to the present disclosure.

Referring to FIG. 18, in various aspects, the control assembly 24 may be a modular unit that can be installed on various support apparatuses 100. This configuration may be advantageous for upgrading support apparatuses 100 to include the control assembly 24. In the illustrated example, the control assembly 24 includes the housing 46 and is coupled to the base support 284 of the stretcher 104. The stretcher 104 may include an opening 310 or recess for receiving the housing 46. The control assembly 24 may include a single tether 30 or may include the first and second subassemblies 180, 182 with both the first and second tethers 222, 240. Further, the tethers 30, 222, 240 may be routed through the siderails 116, 118, 120, 290, 292 or may extend around the siderails 116, 118, 120, 290, 292 or otherwise routed to the coverlet 130. The modular control assembly 24 may be coupled or installed onto any configuration of the frame assembly 12 or the support apparatus 100 to provide the air and power to the surface assembly 16, as well as provide the tethers 30, 222, 240.

With reference to FIGS. 7-18, the winches 188, 194 may be configured to rotate to assist in moving the coverlet 130 in different directions. In such examples, the control assembly 24 may include a motor assembly 314, which is configured to rotate at least a respective winch 188, 194. The blowers 184, 190 and the power sources 186, 192 may remain stationary or may be included in the housing 46 with the winches 188, 194 and are, consequently, rotated by the motor assembly 314. The rotation of the winches 188, 194 does not substantially impede the function of the blowers 184, 190 and the power sources 186, 192 for providing air and power to the coverlet 130. Further, the tethers 222, 240 may be removed from the siderails 116, 118, 120, 290, 292 or remain in the siderails 116, 118, 120, 290, 292 and rerouted around the support apparatus 100 to adjust the coverlet 130 in different directions. Additionally or alternatively, additional tethers 222, 240 operably coupled with the motor assembly 314 may be added to the control assembly 24 to couple with the coverlet 130 at additional locations.

With reference to FIG. 19, as well as FIGS. 9-18, a method 320 for transferring a patient between support apparatuses 100 includes step 322 of providing the coverlet 130 on the first support apparatus 100, which includes the support surface system 14. The coverlet 130 is positioned on the frame assembly 12 and the patient is supported on the coverlet 130. In step 324, the coverlet 130 is coupled to the control assembly 24 of the first support apparatus 100 via the respective tether 222, 240. Accordingly, the control assembly 24 of the first support apparatus 100 provides air and power to the coverlet 130 to provide climate management, such as the MCM layer 38 and temperature regulation.

In step 326, the coverlet 130 is coupled with the control assembly 24 of the second support apparatus 100 via the respective tether 222, 240. The second support apparatus 100 includes the support surface system 14 and is disposed adjacent to and aligned with the first support apparatus 100. The control assembly 24 of the first support apparatus 100 may be deactivated. In step 328, the control assembly 24 of the of the first support apparatus 100 is disengaged from the coverlet 130.

In step 330, the control assembly 24 of the second support apparatus 100 is activated to provide the air and power to the coverlet 130. In step 332, the re-directing valve 60 on the second support apparatus 100 is adjusted to direct the airflow through the bottom surface 64 of the coverlet 130 to provide the "hover" effect. In step 332, one of the winches 188, 194 of the second support apparatus 100 associated with the respective tether 222, 240 coupled to the coverlet 130 is activated. The respective winch 188, 194 applies tension and a pull force to the coverlet 130. In step 332, the coverlet 130 and the patient are moved by the caregiver, using the "hover" effect and the respective tether 222, 240 to the second support apparatus 100. The patient and the coverlet 130 are now fully positioned on the second support apparatus 100.

In step 334, the re-directing valve 60 of the second support apparatus 100 is adjusted, and the air is redirected through the spacer material 18 to form the MCM layer 38 and provide treatment to the patient. In step 336, the current is driven through the thermoelectric device 20 to provide heating and/or cooling for the patient. The steps 322-336 of the method 320 may be repeated, omitted, performed concurrently, etc. without departing from the teachings herein.

With reference to FIGS. 1-19, according to various aspects, when the control assembly 24 is integrated into the support apparatus 100 the controller 200 of the support apparatus 100 is configured to control the support surface system 14. In examples where the support surface system 14 is a separate or removable system, the designated controller 160 of the support surface system 14 is configured to control the support surface system 14. In certain aspects, the controller 200 of the support apparatus 100 may be in communication with the designated controller 160 of the support surface system 14 to allow the caregiver to input information through the user interface 170, 210 on the support apparatus 100 to control the support surface system 14. In such examples, the controller 200 receives a control command from the user interface 170, 210 and communicates the command to the controller 160 of the support surface system 14, which consequently controls the control assembly 24 accordingly.

The controllers 160, 200 may be configured to communicate via wired and wireless communication protocols. In various examples, coupling the support surface system 14 to the support apparatus 100, such as in the configuration illustrated in FIG. 16, may provide for wired communication between the support surface system 14 and the support apparatus 100. In such examples, each of the support surface system 14 and the support apparatus 100 have mating communication connectors that engage one another to provide wired communication therebetween.

In additional or alternative configurations, the controller 200 of the support apparatus 100 is configured to communicate with the controller 160 of the support surface system 14 via a wireless communication network. The communication network may be part of a network of the medical facility, which may include a combination of wired connections (e.g., Ethernet), as well as wireless connections, which may include the wireless communication network. The communication network may include a variety of electronic devices, which may be configured to communicate over various wired or wireless communication protocols. The communication network may include a wireless router through which the remotely accessed devices may be in communication with one another as well as a local server.

The communication network may be implemented via one or more direct or indirect nonhierarchical communication protocols, including but not limited to, Bluetooth®, Bluetooth® low energy (BLE), Thread, Ultra-Wideband, Z-wave, ZigBee, etc. Additionally, the communication network may correspond to a centralized or hierarchal communication network where one or more of the devices communicate via the wireless router (e.g., a communication routing controller). Accordingly, the communication network may be implemented by a variety of communication protocols, including, but not limited to, global system for mobile communication (GSM), general packet radio services, code division multiple access, enhanced data GSM environment, fourth generation (4G) wireless, fifth generation (5G) wireless, Wi-Fi, world interoperability for wired microwave access (WiMAX), local area network, Ethernet, etc. By flexibly implementing the communication network, the various devices and servers may be in communication with one another directly via the wireless communication network, or cellular data connection.

In certain aspects, the support apparatus 100 and/or the support surface system 14 may be capable of communicating wirelessly via a wireless communication module. The wireless communication module generally communicates via an SPI link with circuitry associated with the support apparatus 100 (e.g., the communication circuitry 208) or the support surface system 14 (e.g., communication circuitry 168) and the wireless 802.11 link with wireless access points. The wireless access points are generally coupled to Ethernet switches via 802.3 links. It is contemplated that the wireless communication modules may communicate with the wireless access points via any of the wireless protocols disclosed herein. Additionally or alternatively, the Ethernet switches may generally communicate with Ethernet via 802.3 link. Ethernet is also in communication with the local server, allowing information and data to be communicated between support surface system 14 and the support apparatus 100.

Referring still to FIGS. 1-19, the support surface assembly 16 provides treatment to the patient. More conventional surfaces, such as foam mattresses, can lead to skin breakdown for patients positioned on such surfaces for extended periods. Additionally, patient transfers between support apparatuses 100 can aggravate skin breakdown by exposing the skin of the patient to shear forces. The support surface system 14 provides the MCM layer 38 working with a thermoelectric heating and cooling system (i.e., the thermoelectric device 20) for optimal skin climate. Each of the blowers 26, 184, 190 and the power sources 28, 186, 192 may operate at different strengths or power levels to provide different treatments to the patient. For example, the blowers 26, 184, 190 may be configured to operate in high-volume and low-volume modes. In such examples, different levels of moisture wicking may be accomplished. Further, a buildup of air to increase pressure for the high-volume mode may accomplish a short burst of high-volume airflow to assist in the "hover-like" effect for the transfer. Further, the voltage applied to the thermoelectric device 20 may be varied to selectively drive heating and/or cooling at different levels for treatment and patient comfort.

Moreover, the support surface system 14 transfers with the patient and assists the caregiver in the patient transfer. With more conventional surfaces, caregivers can place themselves at risk of injury when transferring patients, especially bariatric patients. The support surface system 14 provides the caregiver with the surface assembly 16 that can more easily move from one support apparatus 100 to another utilizing the air "hover" capability. With the coverlet 130, the coverlet 130 also includes handles 134 to provide an ergonomic hold location to assist in controlling the transfer of the patient and the coverlet 130.

Use of the present device may provide a variety of advantages. For example, the surface assembly 16 can support a patient for extended periods of time and provide treatment, such as moisture wicking and temperature regulation. Additionally, the surface assembly 16 can assist in reducing adverse effects, such as skin breakdown, for patients and reduce injury risk for caregivers. Further, the support surface system 14 includes the tethers 222, 240 and the "hover-like" capability to assist with the patient transfer. Moreover, the support surface system 14 provides the surface assembly 16 that stays with the patient, providing continued treatment to the patient. Moreover, the support surface system 14 includes both the MCM layer 38 and the thermoelectric device 20 for cooling and heating to provide optimal skin climate. Additional benefits or advantages may be realized and/or achieved.

Each of the controllers 36, 160, 200 disclosed herein may include various types of control circuitry, digital or analog, and may each include a processor, a microcontroller, an application specific integrated circuit (ASIC), or other circuitry configured to perform the various inputs or outputs, control, analysis, or other functions described herein. The memories 164, 204 described herein may be implemented in a variety of volatile and nonvolatile memory formats. Routines 166, 206 may include operating instructions to enable the various methods described herein.

The system disclosed herein is further summarized in the following paragraphs and is further characterized by combinations of any and all of the various aspects described therein.

According to one aspect of the present disclosure, a patient support system includes a frame assembly. A support surface system is selectively supported by the frame assembly and configured to support a person thereon. The support surface system includes a surface assembly including a spacer material and a thermoelectric device within an interior of the surface assembly and a control assembly including a blower and a power source. A tether is coupled to the control assembly and the surface assembly. The tether includes an airflow channel in fluid communication with the blower and an interior of the surface assembly. The tether includes an electrical connection operably coupled with the power source and the thermoelectric device. A controller is communicatively coupled to the support surface system. The controller is configured to selectively activate the blower to direct air through the airflow channel and through the spacer material to form a microclimate management layer in the surface assembly and selectively activate the power source to drive a current through the thermoelectric device for temperature regulation.

According to another aspect of the present disclosure, a support surface system further includes a winch operably coupled to a tether. A controller is configured to activate the winch to provide a pull force on the tether.

According to another aspect of the present disclosure, a controller is configured to activate a power source to drive a current through a thermoelectric device in a first direction to provide cooling and in a second direction to provide heating.

According to another aspect of the present disclosure, a frame assembly includes a lift system and a sling bar. A surface assembly is configured as a lift aid.

According to another aspect of the present disclosure, a frame assembly includes at least one of an upper frame and a deck on which a surface assembly is configured to be disposed. The surface assembly is configured as a coverlet.

According to another aspect of the present disclosure, a frame assembly is included in a first support apparatus. A patient support system also includes a second support apparatus, a second control assembly including a blower, a power source, and a winch, and a second tether coupled to the second control assembly and configured to selectively couple to a surface assembly. The second tether includes an airflow channel for directing air from the blower of the second control assembly to an interior of the surface assembly and an electrical connection coupling the power source of the second control assembly to a thermoelectric device.

According to another aspect of the present disclosure, heat is exhausted by directing the heat through at least one of an air-permeable outer ticking of a coverlet, holes defined in a bottom surface of the coverlet, and designated vents in the coverlet.

According to another aspect of the present disclosure, a frame assembly includes an upper frame. A surface assembly is configured as a coverlet selectively disposed on the upper frame.

According to another aspect of the present disclosure, a control assembly is integrated into an upper frame.

According to another aspect of the present disclosure, a siderail is operably coupled to a frame assembly. A tether extends through the siderail. The siderail defines a recessed region for stowing an end of the tether.

According to another aspect of the present disclosure, a frame assembly includes an upper frame, and a control assembly further includes a winch coupled to a lower surface of an upper frame. A tether extends from the winch, through a siderail, and to proximate to an upper surface of the upper frame.

According to another aspect of the present disclosure, a control assembly includes a housing. A frame assembly includes a base support. The housing is selectively coupled to the base support.

According to another aspect of the present disclosure, a frame assembly includes a deck and a base support. A surface assembly is configured as a coverlet selectively disposed on the deck.

According to another aspect of the present disclosure, a patient support system includes a support apparatus including a frame assembly. A control assembly is coupled to the frame assembly. The control assembly includes a blower, a power source, and a winch. A coverlet is selectively disposed on the frame assembly. The coverlet includes a spacer material and a thermoelectric device. A tether is coupled to the control assembly and selectively coupled to the coverlet. The tether includes an airflow channel for directing air from the blower to an interior of the coverlet and an electrical connection coupling the power source with the thermoelectric device. A controller is communicatively coupled to the control assembly. The controller is configured to activate the blower to direct the air through the airflow channel and through an interior of the coverlet, activate the power source to drive a current through the thermoelectric device, and activate the winch to move the coverlet relative to the frame assembly.

According to another aspect of the present disclosure, a valve is in fluid communication with an airflow channel. The valve is configured to redirect air in a first airflow path through a spacer material to form a microclimate management layer and in a second airflow path through a bottom surface of a coverlet to provide a hover effect.

According to another aspect of the present disclosure, a tether includes a connector end configured to engage a connection feature on a coverlet to provide air and power to the coverlet.

According to another aspect of the present disclosure, a support apparatus includes a siderail, and a tether extends through the siderail.

According to another aspect of the present disclosure, a support apparatus includes a base support defining an opening, and a control assembly includes a housing disposed within the opening.

According to another aspect of the present disclosure, a coverlet includes connection features on opposing sides thereof for engaging a tether.

According to another aspect of the present disclosure, a coverlet includes handles at a head end and handles at a foot end.

According to another aspect of the present disclosure, a thermoelectric device includes multiple thermoelectric modules, and a controller is configured to selectively and independently control each thermoelectric module.

According to another aspect of the present disclosure, a thermoelectric device has a first side proximate to a patient and a second side spaced from the patient. A controller is configured to: activate a power source to drive a current through the thermoelectric device in a first direction to provide cooling with the first side, where the second side is configured to generate heat when the current is driven in the first direction; activate the power source to drive the current through the thermoelectric device in a second direction to provide heating with the first side; and activate a blower to direct air proximate the thermoelectric device to exhaust heat when the second side generated heat.

According to another aspect of the present disclosure, a patient support system includes a first support apparatus. A coverlet includes a spacer material and a thermoelectric device. The coverlet is selectively disposed on the first support apparatus. The second support apparatus includes a control assembly including a blower, a power source, and a winch. A tether is coupled to the control assembly and configured to selectively couple to the coverlet. The tether includes an airflow channel for directing air from the blower to an interior of the coverlet and an electrical connection coupling the power source to the thermoelectric device. A controller is communicatively coupled to the control assembly. The controller is configured to activate the winch to provide a pulling force on the coverlet to move the coverlet from the first support apparatus to the second support apparatus.

According to another aspect of the present disclosure, a second support apparatus includes a valve in fluid communication with an airflow channel. The valve is configured to redirect air toward a first support apparatus to produce a hover effect for a coverlet.

According to another aspect of the present disclosure, a tether includes a connector end for selectively engaging a connection feature of a coverlet to provide air and power from a control assembly.

According to another aspect of the present disclosure, air is directed through a spacer material to form a microclimate management layer in a coverlet.

According to another aspect of the present disclosure, a power source is configured to drive a current through a thermoelectric device in a first direction to provide cooling and in a second direction to provide heating.

According to another aspect of the present disclosure, a patient support apparatus includes a frame assembly. A first control subassembly is coupled to the frame assembly on a first side. The first control subassembly includes a first tether including an airflow channel and an electrical connection. A first blower is configured to direct air through the airflow channel. A first power source is configured to drive a current through the electrical connection. A first winch is coupled to the first tether and configured to adjust the first tether. A second control subassembly is coupled to the frame assembly on a second side. The second control subassembly includes a second tether including an airflow channel and an electrical connection. A second blower is configured to direct air through the airflow channel of the second tether. A second power source is configured to drive a current through the electrical connection of the second tether. A second winch is coupled to the second tether and configured to adjust the second tether.

According to another aspect of the present disclosure, a support apparatus includes a first siderail operably coupled to a first side of a frame assembly, and a first tether extends through the first siderail. A second siderail is operably coupled to a second side of the frame assembly, and a second tether extends through the second siderail.

According to another aspect of the present disclosure, a coverlet is selectively disposed on the frame assembly. The coverlet includes a spacer material and a thermoelectric device.

According to another aspect of the present disclosure, a first blower is configured to direct air through a spacer material to form a microclimate management layer when a first tether is coupled to a coverlet.

According to another aspect of the present disclosure, a first power source is configured to drive a current through a thermoelectric device to provide temperature regulation when a first tether is coupled to a coverlet.

According to another aspect of the present disclosure, a first blower is configured to direct air through a spacer material to form a microclimate management layer when a first tether is coupled to a coverlet, and a first power source is configured to drive a current through a thermoelectric device to provide temperature regulation when the first tether is coupled to the coverlet.

According to another aspect of the present disclosure, a controller is configured to activate a power source to drive a current through a thermoelectric device in a first direction to provide cooling and in a second direction to provide heating.

According to another aspect of the present disclosure, a thermoelectric device has a first side proximate to a patient and a second side spaced from a patient. A controller is configured to activate a blower to direct air proximate the thermoelectric device and exhaust heat when the second side is heated.

According to another aspect of the present disclosure, heat is exhausted by directing the heat through at least one of holes defined in a bottom surface of an outer covering, the outer covering that is air permeable, and designated vents.

According to another aspect of the present disclosure, a support surface system includes a surface assembly, including an outer covering, a spacer material disposed within the outer covering, and a thermoelectric device is disposed within the outer covering. A control assembly is operably coupled to the surface assembly. The control assembly includes a blower and a power source. A tether includes an airflow channel in fluid communication with the blower and an interior of the outer covering and an electrical connection in communication with the power source and the thermoelectric device. A controller is communicatively coupled to the control assembly. The controller is configured to selectively activate the blower to direct air through the airflow channel and through the spacer material to form a microclimate management layer in the surface assembly and selectively activate the power source to drive a current through the thermoelectric device for temperature regulation.

According to another aspect of the present disclosure, a method of transferring a patient between support apparatuses includes providing a coverlet on a first support apparatus; coupling the coverlet with a control assembly of a second support apparatus, the control assembly including a blower, a power source, and a winch, wherein the second support apparatus is disposed adjacent to the first support apparatus; directing an airflow from the blower through a bottom surface of the coverlet; activating the winch to provide a pull force on the coverlet to move the coverlet from the first support apparatus to the second support apparatus; redirecting the airflow through a spacer material of the coverlet to form a microclimate management layer; and driving a current through a thermoelectric device of the coverlet to provide temperature regulation.

A means for supporting a patient includes a support frame means and a surface engagement means selectively supported by the support frame means and configured to support a person thereon. The surface engagement means includes a spacer means and a thermoelectric means, a control means including an air directing means and a power providing means, and a coupling means coupled to the control means and the surface engagement means. The coupling means includes an airflow channel in fluid communication with the air directing means and an interior of the surface engagement means and an electrical connection operably coupled with the power providing means and the thermoelectric means. An additional control means is communicatively coupled to the surface engagement means and is configured to selectively activate the air directing means to direct air through the airflow channel and through the spacer means to form a microclimate management layer and selectively activate the power providing means to drive a current through the thermoelectric means for temperature regulation.

It will be understood by one having ordinary skill in the art that construction of the described disclosure and other components is not limited to any specific material. Other exemplary embodiments of the disclosure disclosed herein may be formed from a wide variety of materials, unless described otherwise herein.

For purposes of this disclosure, the term "coupled" (in all of its forms, couple, coupling, coupled, etc.) generally means the joining of two components (electrical or mechanical) directly or indirectly to one another. Such joining may be stationary in nature or movable in nature. Such joining may be achieved with the two components (electrical or mechanical) and any additional intermediate members being integrally formed as a single unitary body with one another or with the two components. Such joining may be permanent in nature or may be removable or releasable in nature unless otherwise stated.

It is also important to note that the construction and arrangement of the elements of the disclosure, as shown in the exemplary embodiments, are illustrative only. Although only a few embodiments of the present innovations have been described in detail in this disclosure, those skilled in the art who review this disclosure will readily appreciate that many modifications are possible (e.g., variations in sizes, dimensions, structures, shapes, and proportions of the various elements, values of parameters, mounting arrangements, use of materials, colors, orientations, etc.) without materially departing from the novel teachings and advantages of the subject matter recited. For example, elements shown as integrally formed may be constructed of multiple parts, or elements shown as multiple parts may be integrally formed, the operation of the interfaces may be reversed or otherwise varied, the length or width of the structures and/or members or connector or other elements of the system may be varied, the nature or number of adjustment positions provided between the elements may be varied. It should be noted that the elements and/or assemblies of the system may be constructed from any of a wide variety of materials that provide sufficient strength or durability, in any of a wide variety of colors, textures, and combinations. Accordingly, all such modifications are intended to be included within the scope of the present innovations. Other substitutions, modifications, changes, and omissions may be made in the design, operating conditions, and arrangement of the desired and other exemplary embodiments without departing from the spirit of the present innovations.

It will be understood that any described processes or steps within described processes may be combined with other disclosed processes or steps to form structures within the scope of the present disclosure. The exemplary structures and processes disclosed herein are for illustrative purposes and are not to be construed as limiting.

What is claimed is:

1. A patient support system, comprising:
a frame assembly, wherein the frame assembly includes a lift system and a sling bar;
a support surface system selectively supported by the frame assembly and configured to support a person thereon, wherein the support surface system includes:
a surface assembly including a spacer material and a thermoelectric device within an interior of the surface assembly, wherein the surface assembly is configured as a lift aid;
a control assembly including a blower and a power source; and
a tether coupled to the control assembly and the surface assembly, wherein the tether includes an airflow channel in fluid communication with the blower and an interior of the surface assembly, and wherein the tether includes an electrical connection operably coupled with the power source and the thermoelectric device; and
a controller communicatively coupled to the support surface system, wherein the controller is configured to:
selectively activate the blower to direct air through the airflow channel and through the spacer material to form a microclimate management layer in the surface assembly; and
selectively activate the power source to drive a current through the thermoelectric device for temperature regulation.

2. The patient support system of claim 1, wherein the support surface system further includes:
a winch operably coupled to the tether, and wherein the controller is configured to activate the winch to provide a pull force on the tether.

3. The patient support system of claim 1, wherein the controller is configured to activate the power source to drive the current through the thermoelectric device in a first direction to provide cooling and in a second direction to provide heating.

4. The patient support system of claim 1, further comprising:
a support apparatus including a second frame assembly and a second surface assembly, the second frame assembly including at least one of an upper frame and a deck on which the surface assembly is configured to be disposed, and wherein the second surface assembly is configured as a coverlet.

5. The patient support system of claim 4, further comprising:
a siderail operably coupled to the second frame assembly, wherein the tether extends through the siderail, and wherein the siderail defines a recessed region for stowing an end of the tether.

6. The patient support system of claim 5, further comprising a second control assembly, wherein the second frame assembly includes the upper frame, and wherein the second control assembly further includes a winch coupled to a lower surface of the upper frame, and further wherein the tether extends from the winch, through the siderail, and to proximate to an upper surface of the upper frame.

7. The patient support system of claim 4, further comprising:
a second support apparatus;
a second control assembly including a blower, a power source, and a winch; and
a second tether coupled to the second control assembly and configured to selectively couple to the surface assembly, wherein the second tether includes an airflow channel for directing air from the blower of the second control assembly to an interior of the surface assembly and an electrical connection coupling the power source of the second control assembly to the thermoelectric device.

8. A patient support system, comprising:
a support apparatus including a frame assembly;
a control assembly coupled to the frame assembly, wherein the control assembly includes a blower, a power source, and a winch;
a coverlet selectively disposed on the frame assembly, wherein the coverlet includes a spacer material and a thermoelectric device;
a tether coupled to the control assembly and selectively coupled to the coverlet, wherein the tether includes an airflow channel for directing air from the blower to an interior of the coverlet and an electrical connection coupling the power source with the thermoelectric device; and
a controller communicatively coupled to the control assembly, wherein the controller is configured to:
activate the blower to direct the air through the airflow channel and through an interior of the coverlet;
activate the power source to drive a current through the thermoelectric device; and
activate the winch to move the coverlet, wherein the coverlet is configured for horizontal transfer to the frame assembly from a second frame assembly of a second support apparatus via the tether and the winch.

9. The patient support system of claim 8, further comprising:
a valve in fluid communication with the airflow channel, wherein the valve is configured to redirect the air in a first airflow path through the spacer material to form a microclimate management layer and in a second airflow path through a bottom surface of the coverlet to provide a hover effect.

10. The patient support system of claim 8, wherein the support apparatus includes a base support defining an opening, and wherein the control assembly includes a housing disposed within the opening.

11. The patient support system of claim 8, wherein the coverlet includes connection features on opposing sides thereof for engaging the tether.

12. The patient support system of claim 8, wherein the coverlet includes handles at a head end and handles at a foot end.

13. The patient support system of claim 8, wherein the thermoelectric device includes multiple thermoelectric modules, and wherein the controller is configured to selectively and independently control each thermoelectric module.

14. The patient support system of claim 8, wherein the thermoelectric device has a first side proximate to a patient and a second side spaced from the patient, and wherein the controller is configured to:
activate the power source to drive the current through the thermoelectric device in a first direction to provide cooling with the first side, wherein the second side is configured to generate heat when the current is driven in the first direction;

activate the power source to drive the current through the thermoelectric device in a second direction to provide heating with the first side; and activate the blower to direct the air proximate the thermoelectric device to exhaust heat when the second side generates heat.

15. The patient support system of claim 14, wherein the heat is exhausted by directing the heat through at least one of an air-permeable outer ticking of the coverlet, holes defined in a bottom surface of the coverlet, and designated vents in the coverlet.

16. A patient support apparatus, comprising:

a frame assembly;

a first control subassembly coupled to the frame assembly on a first side, wherein the first control subassembly includes:

a first tether including an airflow channel and an electrical connection;

a first blower configured to direct air through the airflow channel;

a first power source configured to drive a current through the electrical connection; and a first winch coupled to the first tether and configured to adjust the first tether;

a second control subassembly coupled to the frame assembly on a second side, wherein the second control subassembly includes:

a second tether including an airflow channel and an electrical connection;

a second blower configured to direct air through the airflow channel of the second tether;

a second power source configured to drive a current through the electrical connection of the second tether; and a second winch coupled to the second tether and configured to adjust the second tether; and a coverlet including a spacer material and a thermoelectric device, wherein at least one of the first winch and the second winch is configured to be coupled to the coverlet and provide a pulling force on the coverlet to move the coverlet from a second frame assembly to the frame assembly.

17. The patient support apparatus of claim 16, further comprising:

a first siderail operably coupled to the first side of the frame assembly, wherein the first tether extends through the first siderail; and a second siderail operably coupled to the second side of the frame assembly, wherein the second tether extends through the second siderail.

18. The patient support apparatus of claim 6, wherein the first blower is configured to direct the air through the spacer material to form a microclimate management layer when the first tether is coupled to the coverlet, and wherein the first power source is configured to drive the current through the thermoelectric device to provide temperature regulation when the first tether is coupled to the coverlet.

* * * * *